(12) United States Patent
Edrei et al.

(10) Patent No.: US 12,383,124 B2
(45) Date of Patent: Aug. 12, 2025

(54) SYSTEMS AND METHODS FOR IMAGING A BODY PART DURING A MEDICAL PROCEDURE

(71) Applicant: BEYEONICS SURGICAL LTD, Haifa (IL)

(72) Inventors: Eitan Yehiel Edrei, Haifa (IL); Avi Reuven, Haifa (IL); Eran Segev, Haifa (IL); Shahaf Zommer, Haifa (IL); Ron Schneider, Haifa (IL); Rani Ben-Yishai, Haifa (IL)

(73) Assignee: BEYEONICS SURGICAL LTD, Haifa (IL)

( * ) Notice: Subject to any disclaimer, the term of this patent is extended or adjusted under 35 U.S.C. 154(b) by 0 days.

(21) Appl. No.: 18/967,753

(22) Filed: Dec. 4, 2024

(65) Prior Publication Data
US 2025/0090007 A1    Mar. 20, 2025

Related U.S. Application Data

(63) Continuation of application No. 18/921,386, filed on Oct. 21, 2024, now abandoned, which is a continuation-in-part of application No. 17/287,552, filed as application No. PCT/IL2019/051140 on Oct. 23, 2019.

(30) Foreign Application Priority Data

Oct. 25, 2018   (IL) .......................................... 262619

(51) Int. Cl.
*A61B 1/04* (2006.01)
*A61B 1/00* (2006.01)
*A61B 1/06* (2006.01)

(52) U.S. Cl.
CPC ............ *A61B 1/04* (2013.01); *A61B 1/00048* (2013.01); *A61B 1/06* (2013.01)

(58) Field of Classification Search
CPC .......... A61B 1/04; A61B 1/00048; A61B 1/06
See application file for complete search history.

(56) References Cited

U.S. PATENT DOCUMENTS 6,243,197 B1    6/2001   Schalz
6,475,138 B1 *  11/2002  Schechter ............. A61B 18/20
                                                        606/17

(Continued)

FOREIGN PATENT DOCUMENTS

EP            3285107 A1    2/2018
KR      20160148889 A      12/2016
(Continued)

*Primary Examiner* — Zade Coley
(74) *Attorney, Agent, or Firm* — S.J. Intellectual Property Ltd.

(57) ABSTRACT

Systems and methods for imaging a body part during a medical procedure e.g., by imaging the body part using at least one image capture unit, where the image capture unit is configured to sense light at least in the IR spectrum; illuminating at least a portion of the body part with light in the infrared (IR) spectrum, using at least one IR light source such that IR illumination of at least one of the at least one IR light source is coaxial with an optical axis of one of the at least one image capture unit; and outputting imagery data emanating from the at least one image capture unit for displaying thereof.

13 Claims, 17 Drawing Sheets

(56) References Cited

U.S. PATENT DOCUMENTS

| | | | | |
|---|---|---|---|---|
| 6,830,334 B2* | 12/2004 | Niven | | A61B 3/117 |
| | | | | 351/221 |
| 6,898,004 B2* | 5/2005 | Shimizu | | G02B 21/16 |
| | | | | 359/388 |
| 8,919,960 B2* | 12/2014 | Lewis | | G06T 7/0012 |
| | | | | 351/200 |
| 10,052,162 B2* | 8/2018 | Bai | | H04N 13/254 |
| 2002/0087149 A1 | 7/2002 | McCary | | |
| 2003/0193647 A1* | 10/2003 | Neal | | A61B 3/14 |
| | | | | 351/221 |
| 2005/0171514 A1* | 8/2005 | Van Saarloos | | A61F 9/008 |
| | | | | 606/5 |
| 2010/0201944 A1* | 8/2010 | Lewis | | A61B 3/14 |
| | | | | 351/246 |
| 2011/0172746 A1* | 7/2011 | Porter | | A61N 5/01 |
| | | | | 607/89 |
| 2011/0261184 A1 | 10/2011 | Mason et al. | | |
| 2014/0015948 A1 | 1/2014 | Tam | | |
| 2014/0346957 A1 | 11/2014 | Micucci et al. | | |
| 2016/0262605 A1 | 9/2016 | Taylor et al. | | |
| 2017/0020627 A1* | 1/2017 | Tesar | | A61B 90/361 |
| 2017/0258528 A1* | 9/2017 | Bai | | G02B 23/2484 |
| 2018/0021101 A1 | 1/2018 | Abt | | |
| 2018/0049811 A1 | 2/2018 | Ji et al. | | |
| 2018/0140373 A1 | 5/2018 | Dos Santos et al. | | |
| 2018/0147087 A1 | 5/2018 | Bacher et al. | | |
| 2021/0325649 A1* | 10/2021 | Segev | | A61B 3/0008 |
| 2024/0115120 A1* | 4/2024 | Halderman | | A61B 1/04 |
| 2025/0052990 A1* | 2/2025 | Edrei | | G02B 21/06 |

FOREIGN PATENT DOCUMENTS

| | | | | |
|---|---|---|---|---|
| WO | 2017141187 A1 | 8/2017 | | |
| WO | WO-2020084611 A1 * | 4/2020 | | A61B 1/00048 |

* cited by examiner

SYSTEMS AND METHODS FOR IMAGING A BODY PART DURING A MEDICAL PROCEDURE

TECHNICAL FIELD

The present disclosure generally relates to systems and methods for imaging a body part during a medical procedure.

BACKGROUND

Many ophthalmic devices illuminate visible light for diagnosing or treating ocular pathologies. This illumination might be hazardous to the eyes under prolonged exposures and may also lead to patient discomfort. One of the most common hazards is the hazard of phototoxicity, caused by blue light (visible light in the wavelength band of 380 nm-500 nm) irradiating the retina. International safety standards set recommended limits for the irradiation levels and total energy of this illumination, but also acknowledge the reality that occasionally surgeons or clinicians may have to exceed those limits to complete an examination or procedure.

Other body parts, for example, but not limited to, the brain, may also be sensitive to light (e.g., heat produced by light or phototoxicity) during surgery or other medical procedures. Additionally, illumination is frequently adjusted by a surgeon for other reasons during a medical procedure.

For achieving a good image of at least a portion of a body part being medically treated (e.g., operated), white light illumination of that body part or the portion thereof may not be sufficient.

References considered to be relevant as background to the presently disclosed subject matter are listed below. Acknowledgement of the references herein is not to be inferred as meaning that these are in any way relevant to the patentability of the presently disclosed subject matter.

U.S. Pat. No. 6,898,004 to Shimizu, et al., describes a microscope system wherein illumination light rays are emitted from a light source. The illumination light rays are collimated and reflected from a mirror to the optical element array. The optical element array is located at a conjugate position of a specimen, and includes a plurality of micro mirrors arranged in a matrix form. The micro mirrors are individually controlled to selectively reflect the illumination light rays for illuminating the specimen. Thus, a predetermined pattern of the light rays is reflected from the optical element array to an objective lens. The illumination light rays are projected on the specimen from the objective lens and the specimen is illuminated by the predetermined illumination pattern.

U.S. Pat. No. 6,243,197 to Schalz describes an illuminating device for a microscope, having a light source, an illuminating optical system and an LCD arranged in the illuminating beam path. The illuminating light is directed onto the object from the light source via the LCD, a transparent/opaque pattern being generated on the LCD by means of a control and calculating device. The LCD is arranged in a plane (AP') which is conjugate with respect to the field diaphragm plane or aperture diaphragm plane (AP) and has a planar matrix composed of individual pixels arranged next to one another and of the same dimensions, the pixels each being constructed such that they can be driven individually to generate an arbitrary transparent/opaque pattern. The control and calculating device is constructed as a computer with a graphics card. The graphics card generates the image signal for driving the LCD, it being possible for the image generated on the LCD to be represented simultaneously on a separate monitor.

US Patent Publication serial number 20020087149 of McCary describes an ophthalmic illumination device which includes a source of light that has a spectrum primarily in a red spectrum and is substantially devoid of spectra in any other color, including a blue spectrum and a green spectrum. The red light is provided by a red light emitting diode and may be used in combination with known ophthalmic illumination devices that provide a white light. A surgeon controls the device and can switch between the red light and the white light.

International Patent Publication serial number WO2017141187 of Novartis Ag. describes methods and systems for performing an ophthalmic surgical procedure include pulsed illumination of target tissue. The systems may include an illumination instrument arranged to illuminate tissue at a surgical site during the ophthalmic surgical procedure. A light source provides illumination to the illumination instrument for emission from the illumination instrument toward the surgical site. A controller communicates with the light source and activates the light source to provide illumination pulses at a frequency above the flickering perception in humans and with enough light for cameral exposure and human light perception. The light source pulses to minimize phototoxicity.

BRIEF DESCRIPTION OF THE DRAWINGS

The present disclosure will be understood and appreciated more fully from the following detailed description, taken in conjunction with the drawings in which:

FIG. 13A shows an image of the eye without using IR illumination of the eye; and FIG. 13B shows an image of the eye when using IR illumination of the eye;

DESCRIPTION OF EXAMPLE EMBODIMENTS

Overview

Figure 1A:
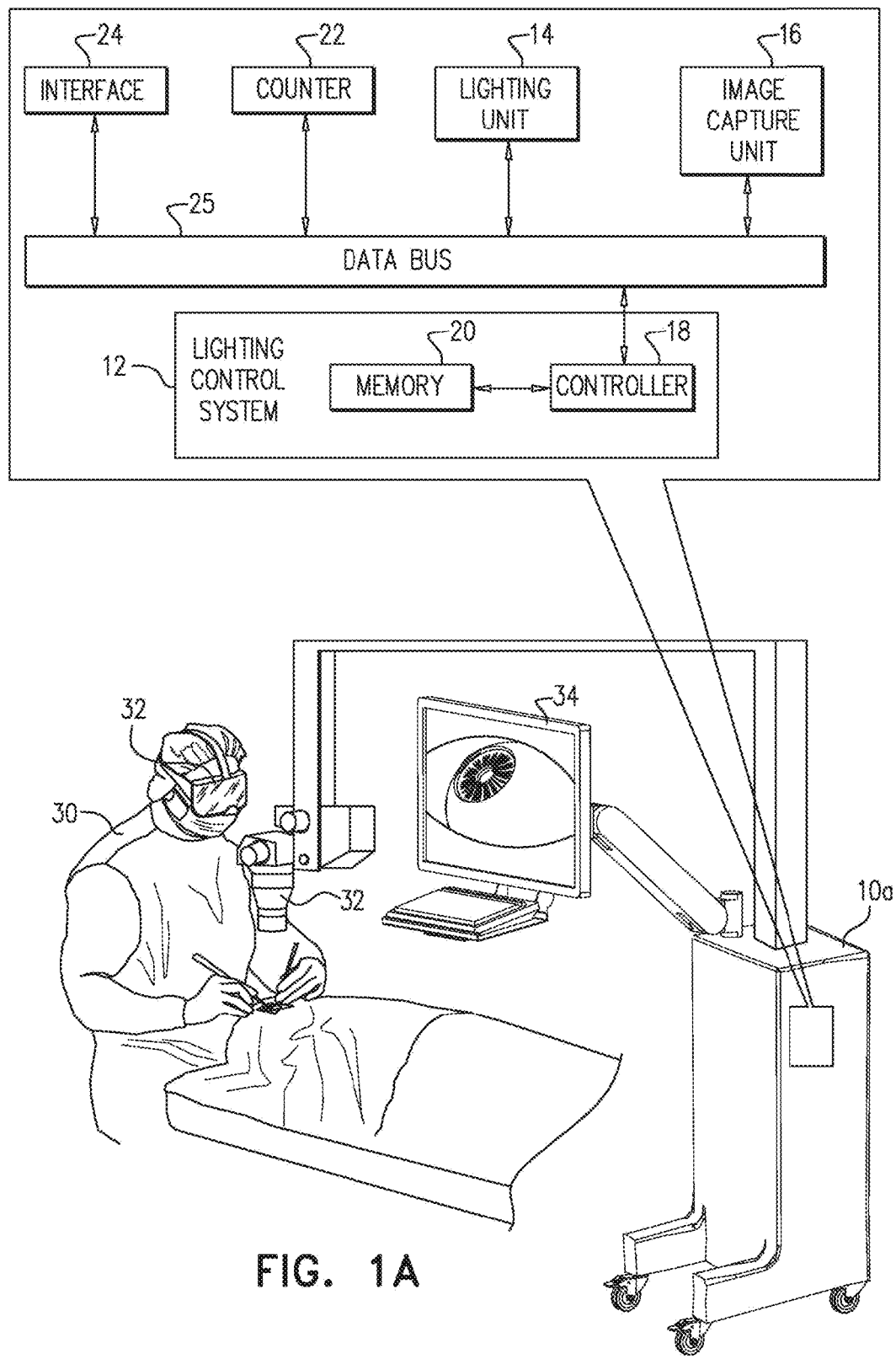
FIGS. 1a and 1b are partly pictorial, partly block diagram views of a surgical microscope system constructed and operative according to embodiments of the present disclosure.

In accordance with a first aspect of the presently disclosed subject matter, there is provided a system for imaging a body part during a medical procedure, the system comprising:
  at least one image capture unit for imaging the body part, the at least one image capture unit configured to sense light at least in the infrared (IR) spectrum;
  at least one IR light source for illuminating a portion of the body part with light in the IR spectrum, wherein IR light emitted by at least one of the at least one IR light source is coaxial with an optical axis of one of the at least one image capture unit,
where the system is configured to output imagery data emanating from the at least one image capture unit for displaying thereof.

According to some embodiments, the system may further include at least one visible light source for illuminating the body part with light in the visible spectrum, wherein the at least one image capture unit comprises any combination of image capture units configured to detect light within the visible and the IR spectral ranges.

According to some embodiments, the system may further be configured to enable manual balancing and/or to automatically balance between visible illumination from the at least one visible light source and IR illumination from the at least one IR light source, at least by controlling the intensity of at least one of the at least one visible light source and at least one of the at least one IR light source.

According to some embodiments, the imagery data may be processed to alter the displayable appearance of one or more images or regions of the images of the imagery data.

The imagery data may be configured for two-dimensional (2D) and/or three-dimensional (3D) display via one or more display devices of one or more displaying types.

The one or more display devices may include one or more of: a head mounted display (HMD); a screen; or a hologram.

According to some embodiments, the system may be embedded in or serving as one of: (i) a mono or a stereoscopic surgical microscope, (ii) a diagnostic microscope, (iii) a slit lamp microscope, (iv) an exoscope, (v) a control interface of a robotic surgery system, and/or (vi) a traditional optical microscope with optical eyepieces.

According to some embodiments, IR light emitted from at least one of the at least one IR light source may be collimated.

According to some embodiments, the body part may include an eye of a subject and wherein the portion of the body part may include, for example, at least one of: a retina, a pupil and/or an area enclosed by a limbus of the eye of the subject.

The medical procedure may be any medical procedure such as a surgery, a cataract surgery, a medical examination, etc.

According to some embodiments, the system may further include a focusing mechanism and/or an aperture adjustment mechanism, for manually and/or automatically adjusting the focus and/or the aperture of the at least one image capture unit in response to or in conjunction with changes in the IR illumination and/or in the visible illumination.

In some embodiments, the IR illumination may be within the near IR (NIR) spectrum.

According to some embodiments, the at least one image capture unit may include one or more of:
  at least one RGB (Red Green Blue) sensor;
  at least one RGB sensor and at least one IR sensor;
  separate sensors for different spectral ranges;
  at least one RGB-IR sensor.

According to some embodiments, the at least one image capture unit may include at least two image capture units for stereoscopic imaging, wherein the at least one IR light source comprises at least two IR light sources, wherein IR light emitted by each of the at least two IR light sources is coaxial with an optical axis of a different one of the at least two image capture units.

In accordance with a second aspect of the presently disclosed subject matter, there is provided a method for imaging a body part during a medical procedure, where the method may include:
  imaging the body part using at least one image capture unit, wherein the image capture unit is configured to sense light at least in the IR spectrum;
  illuminating at least a portion of the body part with light in the infrared (IR) spectrum, using at least one IR light source such that IR illumination of at least one of the at least one IR light source is coaxial with an optical axis of one of the at least one image capture unit; and
  outputting imagery data emanating from the at least one image capture unit for displaying thereof.

According to some embodiments, the method may further include illuminating the body part with light in the visible spectrum using at least one visible light source, wherein the at least one image capture unit comprises any combination of one or more image capture units configured to detect light within the visible and the IR spectral ranges.

Additionally or alternatively, the method may further include enabling manual and/or automatic balancing between visible illumination from the at least one visible light source and IR illumination from the at least one IR light source, at least by controlling the intensity of at least one of the at least one visible light source and/or at least one of the at least one IR light source.

According to some embodiments, the imagery data may be processed to alter the appearance of one or more images or regions of images within the imagery data.

The imagery data may be configured for two-dimensional (2D) and/or three-dimensional (3D) display via one or more display devices of one or more displaying types.

According to some embodiments, the method may further include collimating IR light emitted from at least one of the at least one IR light source.

DETAILED DESCRIPTION

In the following detailed description, numerous specific details are set forth in order to provide a thorough understanding of the presently disclosed subject matter. However, it will be understood by those skilled in the art that the presently disclosed subject matter may be practiced without these specific details. In other instances, well-known methods, procedures, and components have not been described in detail so as not to obscure the presently disclosed subject matter.

In the drawings and descriptions set forth, identical reference numerals indicate those components that are common to different embodiments or configurations.

The terms "computer", "processor", and "controller" should be expansively construed to cover any kind of electronic device with data processing capabilities, including, by way of non-limiting example, a personal desktop/laptop computer, a server, a computing system, a communication device, a smartphone, a tablet computer, a smart television, a processor (e.g. digital signal processor (DSP), a microcontroller, a field programmable gate array (FPGA), an application specific integrated circuit (ASIC), etc.), a group of multiple physical machines sharing performance of various tasks, virtual servers co-residing on a single physical machine, any other electronic computing device, and/or any combination thereof.

In practice, some or all of the functions described herein may be combined in a single physical component or, alternatively, implemented using multiple physical components. These physical components may comprise hard-wired (such as a computer specially constructed for the desired purposes) or programmable devices (such as general-purpose computer specially configured for the desired purpose), or a combination of the two. In some embodiments, at least some of the functions of the processing circuitry may be carried out by a programmable processor under the control of suitable software. This software may be downloaded to a device in electronic form, over a network, for example. Alternatively or additionally, the software may be stored in tangible, non-transitory computer-readable storage media, such as optical, magnetic, or electronic memory. The term "non-transitory" is used herein to exclude transitory, propagating signals, but to otherwise include any volatile or non-volatile computer memory technology suitable to the application.

It is appreciated that software components of the present disclosure may, if desired, be implemented in ROM (read only memory) form. The software components may, generally, be implemented in hardware, if desired, using conventional techniques. It is further appreciated that the software components may be instantiated, for example: as a computer program product or on a tangible medium. In some cases, it may be possible to instantiate the software components as a signal interpretable by an appropriate computer, although such an instantiation may be excluded in certain embodiments of the present disclosure.

As used herein, the phrase "for example," "such as", "for instance" and variants thereof describe non-limiting embodiments of the presently disclosed subject matter. Reference in the specification to "one case", "some cases", "other cases" or variants thereof means that a particular feature, structure or characteristic described in connection with the embodiment(s) is included in at least one embodiment of the presently disclosed subject matter. Thus, the appearance of the phrase "one case", "some cases", "other cases" or variants thereof does not necessarily refer to the same embodiment(s).

Figure 1B:
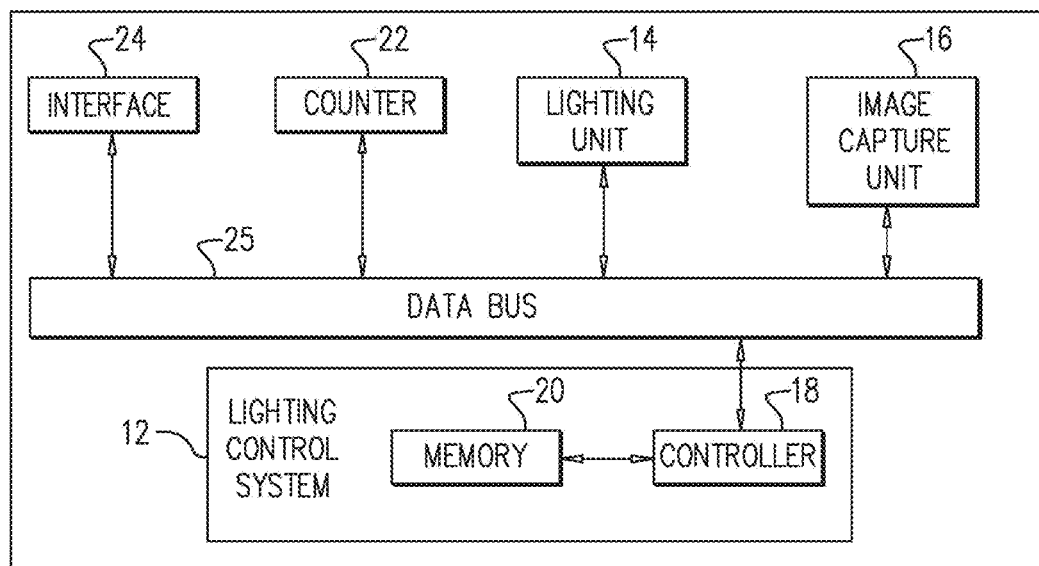
Figure 1B:
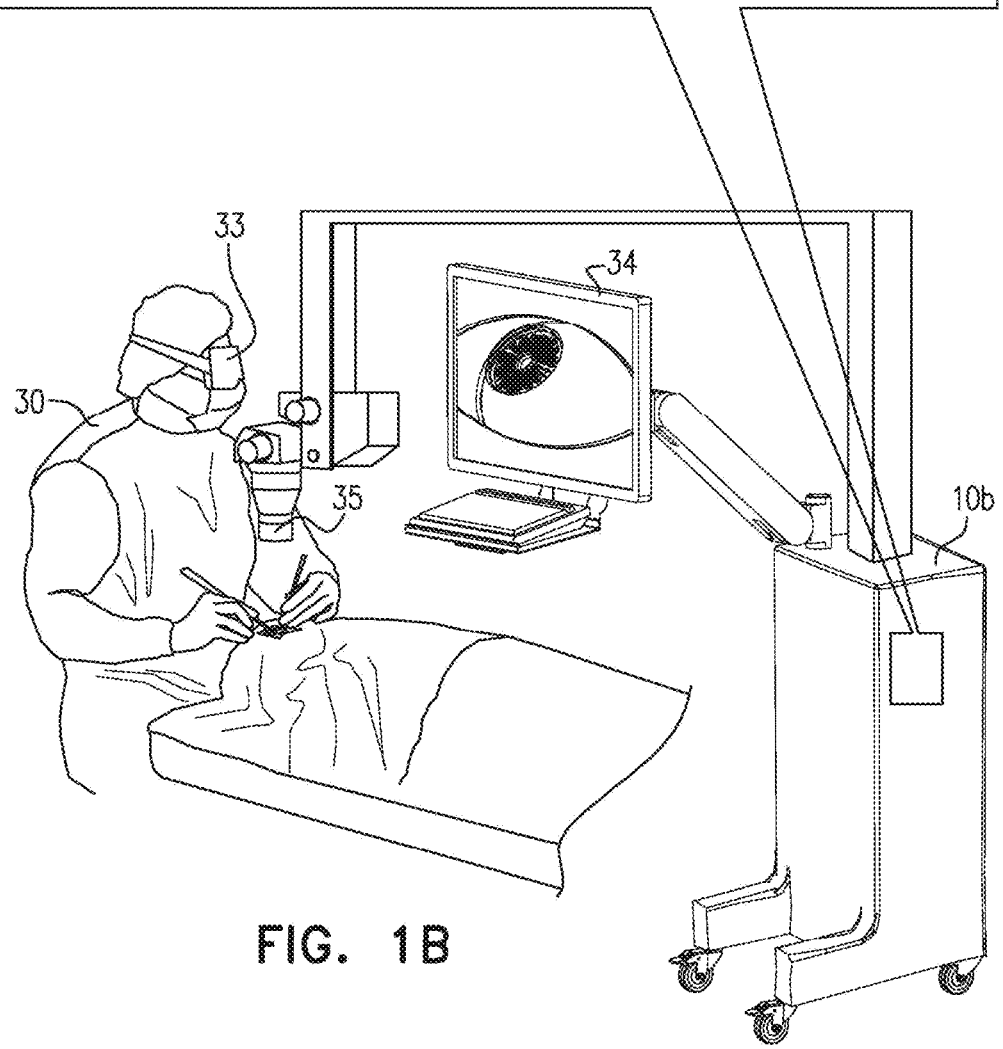

In embodiments of the presently disclosed subject matter, fewer, more and/or different stages than those shown in FIGS. 2, 3, 4, 5, 9 and 10 may be executed. In embodiments of the presently disclosed subject matter one or more stages illustrated in FIGS. 2, 3, 4, 5, 9 and 10 may be executed in a different order and/or one or more groups of stages may be executed simultaneously. FIGS. 1a and 1b illustrates a general schematic of the system architecture according to an embodiment of the presently disclosed subject matter. Each module in FIGS. 1a and 1b may be made up of any combination of software, hardware and/or firmware that performs the functions as defined and explained herein. The modules in FIGS. 1a and 1b may be centralized in one location or dispersed over more than one location. In other embodiments of the presently disclosed subject matter, the system may comprise fewer, more, and/or different modules than those shown in FIGS. 1a and 1b.

It is to be noted that, with reference to each of the flowcharts of FIGS. 2, 3, 4, 5, 9 and 10, some of the blocks can be integrated into a consolidated block or can be broken down to a few blocks and/or other blocks may be added. Furthermore, in some cases, the blocks can be performed in a different order than described herein. It is to be further noted that some of the blocks are optional. It should be also noted that whilst the flowchart is described also with reference to the system elements that realizes them, this is by no means binding, and the blocks can be performed by elements other than those described herein.

Any reference in the specification to a method should be applied mutatis mutandis to a system capable of executing the method and should be applied mutatis mutandis to a non-transitory computer readable medium that stores instructions that once executed by a computer result in the execution of the method.

Any reference in the specification to a system should be applied mutatis mutandis to a method that may be executed by the system and should be applied mutatis mutandis to a non-transitory computer readable medium that stores instructions that may be executed by the system.

Any reference in the specification to a non-transitory computer readable medium should be applied mutatis mutandis to a system capable of executing the instructions stored in the non-transitory computer readable medium and should be applied mutatis mutandis to method that may be executed by a computer that reads the instructions stored in the non-transitory computer readable medium.

Bearing this in mind, reference is now made to FIGS. 1a and 1b, which are a partly pictorial, partly block diagram views of a surgical microscope systems 10a and 10b respectively, both collectively referred to herein as "surgical microscope system 10", constructed and operative according to embodiments of the present disclosure.

Most eye procedures are short and last less than an hour or even half an hour. Nevertheless, illumination levels are high, and the phototoxicity damage to the eye is accumulative and can become substantial even in those short intervals of time. Additionally, exposure to illumination may be extremely uncomfortable for a patient. The surgical microscope system 10 is configured to automatically determine in real-time whether the illumination is actually required, and reduce the damaging and discomforting light in the short time intervals when it is not. The potential reduction using the surgical microscope system 10 may be small, but even small reductions are significant.

It should be noted that when reference is made to illumination herein, it is to illumination controlled by the surgical microscope system 10 only. Various types of eye surgery also involve using fiber light, which is often controlled by a separate system. It is to be noted that although reference is made herein to illumination controlled by the surgical microscope system 10 only, the presently disclosed subject matter is also applicable to controlling illumination originating from other devices that support external control, including, but not limited to, fiber illumination, mutatis mutandis. Such controlling of other types of illumination during any type of surgery that includes illuminating a surgical site is within the scope of the presently disclosed subject matter.

The surgical microscope system 10, as will be described in more detail below, is configured to reduce the potential hazard of light to the eye, with emphasis on phototoxicity hazard to the retina, caused by light that passes through the pupil. Some of the embodiments described herein may also be useful in medical applications other than eye related applications. The thermal effect of illumination may be harmful and operative microscopes have the ability to cause patient morbidity and in extreme cases even skin burn injuries. In some cases, burn injuries have been reported because of xenon microscope lighting, and burn injuries are generally more frequent during neurosurgical or otolaryngology procedures. Few studies have recommended that surgeons be aware of the issue and minimize illumination intensity and operative time.

The surgical microscope system 10 is configured to automatically identify the time periods when harmful illumination can be reduced or completely blocked, and automatically reduce or block the illumination. For example, the illumination of a body part or a part of the body part may be reduced or blocked during periods of time when it is determined or estimated that the surgeon does not need the light, such as when the surgeon chooses to view preoperative imaging data via a display instead of the magnified image of the surgical field, or during periods of time when no motion is detected in the surgical field and/or no surgical tools are present within the surgical field, or during stages of a surgical workflow in which illumination through the pupil, or white light, or illumination in general is not required. By way of another example, when the head-mounted display of the surgeon is pointing away from the general direction of the region of illumination and no motion is detected (e.g., by cameras) in the surgical field (being, during most of the procedure, but not necessarily throughout the entire procedure, the region of illumination), illumination may be reduced or stopped. However, if motion is detected in the region of illumination while the head-mounted display of the surgeon is pointing away from the general direction of the region of illumination, the surgeon may be assumed to be looking to the side while at the same time the nurse may be, for instance, applying eye-drops to the patient's eye and needs the illumination in the surgical field. Other examples are described in more detail below with reference to FIGS. 2-5.

Reducing damaging illumination may be based on dynamically blocking only the light that illuminates the retina or any other sensitive body part (e.g., a part of the brain), in those periods of time when illumination is not required for the surgical procedures. Alternatively, reducing the damaging illumination can be based on switching between illuminating with white light, i.e. light that comprises energy in the entire visible wavelength, and light that does not comprise energy in a harmful spectrum (e.g. light in a blue spectrum is considered more harmful for the retina), or simply reducing the level of white light illumination. Blocking or reducing illumination is described in more detail with reference to FIGS. 6 and 7 below.

The surgical microscope system 10, in addition to being configured to automatically identify the time periods when harmful illumination can be reduced or completely blocked, is also configured to automatically adjust the illumination level for optimizing the surgical workflow and freeing the surgeon from the need to manually adjust the illumination level many times during the procedure. This need arises from the fact that different stages of a surgical procedure require different intensities and different types of illuminations. For example, by estimating the current stage of the surgery, and based upon predetermined levels of illumination suitable for each stage, the surgical microscope system 10 can determine the required levels of flood and/or coaxial illumination and automatically adjust the illumination levels (coaxial illumination is illumination in which light from a light source is diverted by a semi-transparent mirror so it is projected along an optical axis of a viewer or a camera. In some ophthalmic procedures coaxial illumination is used so the user sees light reflected from the retina which allows better visualization of parts of the anterior segment of the eye). Other examples are described in more detail below, e.g. with reference to FIGS. 2-5.

The surgical microscope system 10 includes a lighting control system 12, a lighting unit 14, an image capture unit 16, and a data bus 25. The lighting unit 14 and the image capture unit 16 can be comprised within a camera-head unit 35 suspended above the surgical field. The lighting control system 12 includes a controller 18 and optionally a memory 20. The memory is configured to store data used by the controller 18. The surgical microscope system 10 may optionally include a counter 22 and an interface 24. The lighting control system 12 controls an illumination provided by the lighting unit 14. The lighting control system 12 is described in more detail with reference to FIGS. 2-9. The image capture unit 16 may include optical and/or electronic components to capture images in a field of view. It is to be noted, in this respect, that the live magnified video generated by the image capture unit 16 may be used for the methods described here, for recording the procedure, and for displaying it, e.g. via monitor 34, for the benefit of the staff in the operating room. In addition, the live magnified video may be viewed by the surgeon, e.g. via monitor 34 or via HMD 32. Alternatively, the surgeon may view a non-digital magnified view of the surgical field via an eyepiece or eyepieces, when they are included in surgical microscope system 10. When the surgical microscope system 10 is fully digital the surgeon may not have a non-digital magnified view of the surgical field via an eyepiece, and in some cases the surgical microscope system 10 does not include any eyepiece at all. The surgical microscope may be part of a robotic system which allows the surgeon to view the surgery and control one or more robotic manipulators. Such a system may also provide autonomous movement of the robotic manipulators while the surgeon monitors the procedure for safety reasons, while viewing the surgery through the surgical microscope.

The counter 22 is configured to count radiation incident upon a body part and is described in more detail below with reference to FIGS. 8 and 9. The interface 24 is configured to transfer data between the surgical microscope system 10 and external surgical tools, external displays and/or data systems, for example, but not limited to, a medical data system (not shown) including medical histories of patients.

FIG. 1a shows a surgeon 30 wearing a head-mounted display 32 which is connected to the surgical microscope system 10. The head-mounted display 32 may be connected to the surgical microscope system 10 via a wired or wireless connection. The head-mounted display 32 displays video generated by the surgical microscope system 10 comprising image data and other data (such as overlaid symbols, menus, numerical data, textual data, etc.) generated by the surgical microscope system 10 itself and optionally additional data (in an image form or in any other form, including text, etc.) received by surgical microscope system 10 from other external systems, such as the medical data system, a phacoemulsification machine, an endoscope camera, etc. The additional data can be pre-acquired data, or data acquired or generated in real-time by one or more of the other external systems. The image data includes images captured by the image capture unit 16 and optionally other medical data relating to the patient. The images captured by the image capture unit 16 may be displayed via an external display 34 (e.g., a 2D or 3D monitor). The data bus 25 is configured to connect the various elements of the surgical microscope system 10 for data transfer purposes.

FIG. 1b shows the surgeon 30 wearing three-dimensional glasses 33 which enable viewing three-dimensional images presented on the external display 34 (which, in this embodiment, is a 3D monitor). The external display 34 may display a video generated by the surgical microscope system 10 comprising image data and other data (such as overlaid symbols, menus, numerical data, textual data, etc.) generated by the surgical microscope system 10 itself and optionally additional data (in an image form or in any other form, including text, etc.) received by surgical microscope system 10 from other external systems, such as the medical data system, a phacoemulsification machine, an endoscope camera, etc. As indicated above, the additional data can be pre-acquired data, or data acquired or generated in real-time by one or more of the other external systems. The image data includes images captured by the image capture unit 16 and optionally other medical data relating to the patient. The data bus 25 is configured to connect the various elements of the surgical microscope system 10 for data transfer purposes.

It is to be noted, with reference to FIGS. 1a and/or 1b, that in some embodiments, the surgical microscope system 10 can include eyepiece(s) (not shown) through which a magnification of the surgical field can be viewed. In such cases, the surgeon 30 may choose not to use, or may not be equipped with, the head-mounted display 32 and/or the three-dimensional glasses 33 and/or the external display 34. When eyepiece(s) are provided, the surgical microscope system 10 may also include a proximity sensor to sense a proximity of the surgeon 30 to the eyepiece(s). The function of the proximity sensor is described in more detail with reference to FIGS. 4 and 10 below.

Figure 2:
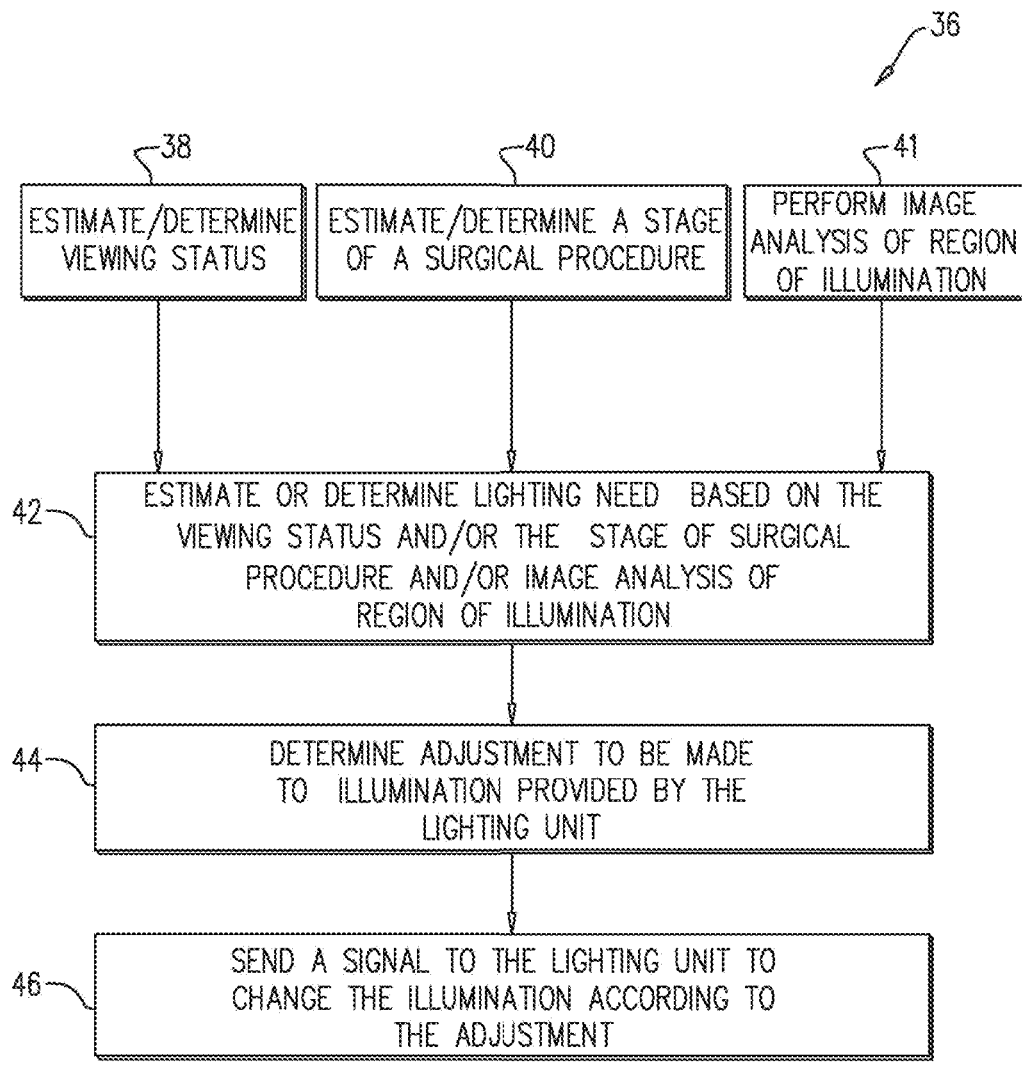
FIG. 2 is a flowchart including exemplary steps in a method of controlling illumination in the surgical microscope system of FIGS. 1a and 1b.

Reference is now made to FIG. 2, which is a flowchart 36 including exemplary steps in a method of controlling illumination in the surgical microscope system 10 of FIGS. 1a and 1b. Reference is also made to FIGS. 1a and 1b. The controller 18 is configured to estimate or determine (block 38) a viewing status of a region of illumination by the surgeon 30. Alternatively, or additionally, the controller 18 is configured to estimate or determine (block 40) a stage of a surgical procedure. Alternatively, or additionally, the controller 18 is configured to perform (block 41) an image analysis related to the region of illumination viewed by at least one sensor (e.g., camera or other imaging device). In some embodiments the outputs of block 38 relating to the viewing status and/or the outputs of block 41 relating to the image analysis are used to estimate or determine the stage of the surgical procedure of block 40. Similarly, in some embodiments the outputs of block 41 relating to the image analysis are used to estimate or determine the viewing status of block 38. Examples of such combinations are included below. It will be appreciated that any suitable combination and/or permutation of the processes of blocks 38, 40 and/or 41 may be implemented.

The controller 18 is configured to estimate or determine (block 42) a lighting need of the surgeon 30 during at least part of the surgical procedure based at least on any one or two or more of the following: (a) the viewing status of the region of illumination by the surgeon 30; (b) the stage of the surgical procedure and a plurality of predetermined lighting needs at a plurality of stages of the surgical procedure; and/or (c) an image analysis related to the region of illumination viewed by at least one sensor.

So, for example, if the lighting need is based on the viewing status of the region of illumination by the surgeon 30, if it is determined or estimated that the surgeon 30 is not looking at the region of illumination, the lighting need may be low or non-existent.

By way of another example, if the lighting need is based on the stage of the surgical procedure, and assuming that a given stage of a given surgical procedure includes removing the surgical microscope system 10 away from the patient's eye and using the surgical microscope system 10 to prepare an intraocular lens for inserting during cataract surgery, the lighting need of such given stage may be in accordance with a predetermined lighting need associated with this stage.

Determination and/or estimation of the lighting need of the surgeon 30 during at least part of the surgical procedure using image analysis is described in more detail with reference to FIG. 3. Determination and/or estimation of the viewing status is described in more detail with reference to FIG. 4. Determination and/or estimation of the stage of the surgical procedure is described in more detail with reference to FIG. 5.

It is to be noted that in some cases, the lighting need estimation can be accompanied by a calculated confidence score, indicative of a confidence level of the estimation.

The controller 18 is configured to determine (block 44) an adjustment to be made to the illumination provided by the lighting unit 14 based on the lighting need. The adjustment may include changing an intensity of the illumination, for example using any one or more of the following: stopping the illumination; adjusting the level of a power source or a current source driving the illumination; adjusting an optical element disposed in the optical path of the lighting unit to change the size of the spot of light; modifying the temporal pattern of the illumination; electrically controlling a permanent liquid crystal shutter disposed in an optical path of the lighting unit; disposing a beam splitter into the optical path or removing it; disposing a digital mirror device into the optical path or removing it; disposing a neutral-density filter into the optical path or removing it, or any suitable combination thereof. The adjustment can additionally or alternatively include changing a spectrum of radiation of the illumination provided by the lighting unit. Changing a spectrum can be performed for example using a filter wheel placed in the optical path of the lighting unit. The adjustment is described in more detail with reference to FIGS. 6 and 7. The controller 18 is configured, in response to determining the adjustment, to send (block 46) a signal to the lighting unit 14 to change the illumination according to the adjustment.

In case the lighting need estimation is accompanied by a calculated confidence score, the confidence score can also be used in the determination of the adjustment. For example, if the confidence score is high (or even full confidence when the lighting need is determined and not estimated), then the adjustment is made accordingly, whereas if the confidence score is low, the adjustment may be determined to be different than the determined estimated lighting need.

Figure 3:
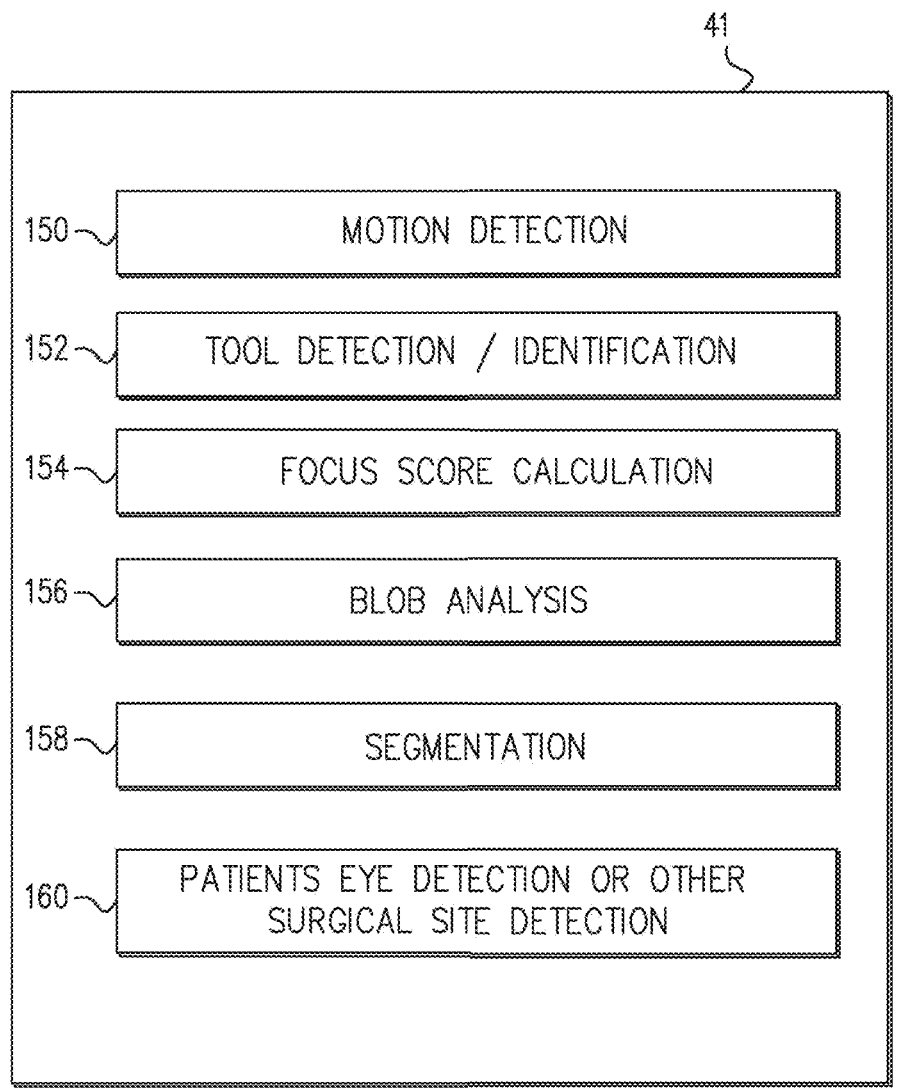
FIG. 3 is a more detailed view of the performing of an image analysis of a region of illumination step.

Reference is now made to FIG. 3, which is a more detailed view of the perform image analysis of a region of illumination step of block 41 of FIG. 2. Reference is also made to FIGS. 1*a* and 1*b*. The image analysis may be used for estimating or determining a lighting need in a variety of ways which may be used independently, or in any suitable combination, to estimate or determine the lighting need. It will be appreciated that other ways for estimating or determining the lighting need may also be used to implement the surgical microscope system 10.

The estimation/determination of the lighting need using image analysis may be based on any one or more of the following inputs, by way of example only: video from cameras generating or capturing a magnified image; video from other cameras (e.g., an infrared (IR) camera for motion detection with IR illumination); and/or image data from modules that generate an image like an intraoperative optical coherence tomography (OCT). It should be noted that the surgeon 30 may be watching a small region-of-interest (ROI) within an entire captured frame, but image analysis generally may have access to the entire captured frame. It should be noted that the various cameras and imaging devices may be capturing different size regions or the same size regions.

Outputs from the image analysis functions may include specific scores/results, and optionally corresponding confidence scores, calculated by any one or more of the following modules or methods: motion detection, histogram data analysis, tool detection and/or identification, a focus score calculation, blob analysis, segmentation, and/or detection of a patient's eye or other surgical sites to detect whether the surgical field is in the image or not. It will be appreciated that other image analysis functions/modules may be used, and the above are only brought by way of example only. Some of the image analysis functions are described in more detail below with reference to FIG. 4 and FIG. 5 where image analysis functions may also be used as part of determining and/or estimating the viewing status and/or the stage of the surgical procedure.

It should be noted that the outputs may include time stamps so that timings and durations may be used in estimating or determining the lighting need of the surgeon 30. For example, in estimating or determining the lighting need of the surgeon 30, if it may be determined that the head-mounted display 32 is pointing away from the region of illumination and additionally there is no motion in the region of illumination for five consecutive seconds, then it may be estimated that lighting is not required.

The following is an example of using motion detection for determining a lighting need of the surgeon 30. For this purpose, the controller 18 may be configured to detect motion in the region of illumination (block 150). Lack of motion for more than a given time period (e.g., 5 seconds) may indicate that illumination may be reduced. It is to be noted that in order to be able to perform motion detection, or any other type of image analysis, a certain amount of light is required. Therefore, in some cases, at least some level or type of illumination is provided when capturing images that are later analyzed by the presently disclosed system. It is to be further noted that the camera used for motion detection may be an IR camera that may also have a dedicated IR illumination, and may cover a region of interest that is larger than the visible-light region of illumination. This may allow the surgical microscope system 10 to detect motion, e.g. a tool about to enter the visible-light region of illumination, before it actually enters the region of interest that is seen by the surgeon, and adjust the illumination without delay. It is to be noted that although reference is made herein to motion detection using image analysis, motion detection can be performed using also other types of motion detection sensors know in the art, or, for example, if the tool is under the control of a robotic system the robot controller may simply inform the microscope of the movements or lack thereof via the data bus.

The following is an example of using tool detection and/or identification for determining a lighting need of the surgeon 30. For this purpose, the controller 18 may be configured to detect a presence or an absence of surgical tools in, and generally around, the region of illumination (block 152). Disappearance of surgical tools from, and from generally around, the region of illumination, may indicate that illumination may be changed (e.g. reduced). Re-appearance of a surgical tool in, and generally around, the region of illumination, may indicate that the illumination should be again changed (e.g. returned to the previous state prior to disappearance of the surgical tool). As long as surgical tools are present in, and generally around, the region of illumination, it may indicate that illumination should be kept unchanged.

However, in some cases, in response to finding a tool(s) in, and generally around, the region of illumination, the controller 18 may be configured to reduce the illumination in, and optionally around, the region of illumination or modify a spatial pattern of the illumination to reduce or remove illumination in a region of the tool(s) to reduce saturation of the image based on glare produced by the tool(s). Modifying a spatial pattern is described in more detail with reference to FIGS. 6 and 7.

The following is an example of using a focus score (optionally in conjunction with motion detection and tool detection) in the image analysis processing for determining a lighting need of the surgeon 30. For this purpose, the controller 18 may be configured to calculate a focus score indicating whether or not the region of illumination is in focus (block 154). It should be noted that for this example it is assumed that the surgical microscope system 10 does not support an auto-focus function, or that the auto-focus function is disabled (i.e. focus is manually adjusted by the surgeon). In the example, the surgeon 30 moves the microscope system 10 away from the surgical field but still over the patient's body. The surgeon 30 takes off the head-mounted display 32 and the image is not in focus for a long time. The illumination may generate a burn on the patient's skin. It should be noted that there may still be movement in the image if the actions of the surgeon 30 outside the region of illumination are moving the patient. A determination that the surgeon 30 is not wearing the head-mounted display 32 in addition to a determination of a low confidence that relevant motion is performed within the images (e.g., if there is motion in the images, but nothing that resembles a tool in the image, then the motion detection confidence may be low as the motion is less likely relevant) in addition to no focus may indicate that lighting is not required.

Predefined time thresholds may be used in relation to adjusting the illumination. For instance, the controller 18 may be configured so that no motion is detected for more than a given time period (e.g., 5 seconds) before illumination is reduced. By way of another example, the controller 18 may immediately reduce illumination (zero seconds waiting period) if the surgeon 30 chooses to view preoperative data via the head-mounted display 32. In general, any combination of scenarios may have its own predefined time thresholds after which the illumination may be adjusted. Moreover, different levels of algorithmic confidence regarding the estimated viewing status or stage or any of the image analysis functions may have different time thresholds. For instance, in the skin burn example given above, the controller 18 may be configured so that non-viewing in addition to a low confidence of motion, in addition to no focus, may be associated with a given waiting period (e.g., one-minute waiting period) before reducing illumination.

The following is an example of using blob analysis for determining a lighting need of the surgeon 30. For this purpose, the controller 18 may be configured to perform blob analysis (block 156) (blobs are connected regions in the image having similar properties). Blob analysis may be implemented to detect saturated areas in the image. Reflection of the illumination from a patient's eye may generate a detectable pattern of small blobs, and therefore the existence of such a pattern may be used for detecting an eye in the image (or more specifically an external part of an eye, as opposed to an internal part thereof). In general, blobs that have shapes and/or sizes that meet certain rules (e.g. their number of pixels is larger than a threshold), or existence of a number of blobs above a threshold, or existence of a certain pattern of blobs, or a certain blob dynamics over a plurality of frames (e.g. a certain blob size increases or a blob moves), or location of a blob, may be used in various ways, such as for detecting a patient's eye, for detecting tools in general or specific tools, for detecting motion in the illuminated region, and for determining a stage in the procedure.

For example, detection of a blob having identifiable shape and size (i.e. the height of the microscope above the eye is always the same, hence the size of a tool in the image will always be similar) at the bottom of an analyzed image and detection of movement thereof at subsequently analyzed images (i.e. blob dynamics over consecutive frames) towards the edge of the cornea (which is identified for instance by segmentation) may indicate a stage in the procedure in which the surgeon is performing a wide cut in the cornea. This stage may require that the illumination is best fitted for the region of the cut, even if on the expense of less-than-optimal illumination at other regions in the image. For instance, the illumination may be reduced to avoid saturation due to reflections from the flat tool the surgeon is using, although this might cause other regions in the image to appear dark. The end of this stage may be indicated by the disappearance of the tool. It is to be noted that each surgeon may operate differently (e.g. an operation conducted by a first surgeon may include stages that are not performed, or are performed differently, by another surgeon), use different tools, etc., and these may be learned so the stage-determination may be personalized.

The following is an example of using segmentation for determining a lighting need of the surgeon 30. For this purpose, the controller 18 may be configured to perform segmentation analysis (block 158). Segmentation can be used to partition an analyzed image into separate entities (e.g. based on grey level and/or color and/or texture and/or shape, etc.)—pupil, iris, blood vessel, tool, finger, etc. It may be used for example for detecting an eye in the image. Additionally, when segments with the expected shapes and sizes of a pupil and iris are detected but blood vessels are not detected, it may indicate that the illumination is too high or too low. Furthermore, sequential segmentation results (obtained for example by performing segmentation analysis of a sequence of consecutively acquired images) may be used to estimate movement of a tool within the region of illumination.

The following is an example of using patient's eye detection or another surgical site detection for determining a lighting need of the surgeon 30. For this purpose, the controller 18 may be configured to perform patient's eye detection or another surgical site detection (block 160). Any appearance or disappearance (i.e. change in the detection status) of the patient's eye or another surgical site in the region of illumination may indicate that the lighting need changed. For instance, if the eye disappeared and a tool appeared it might indicate that the illumination should be decreased, and if the eye reappeared then it might indicate that the illumination should be increased.

Figure 4:
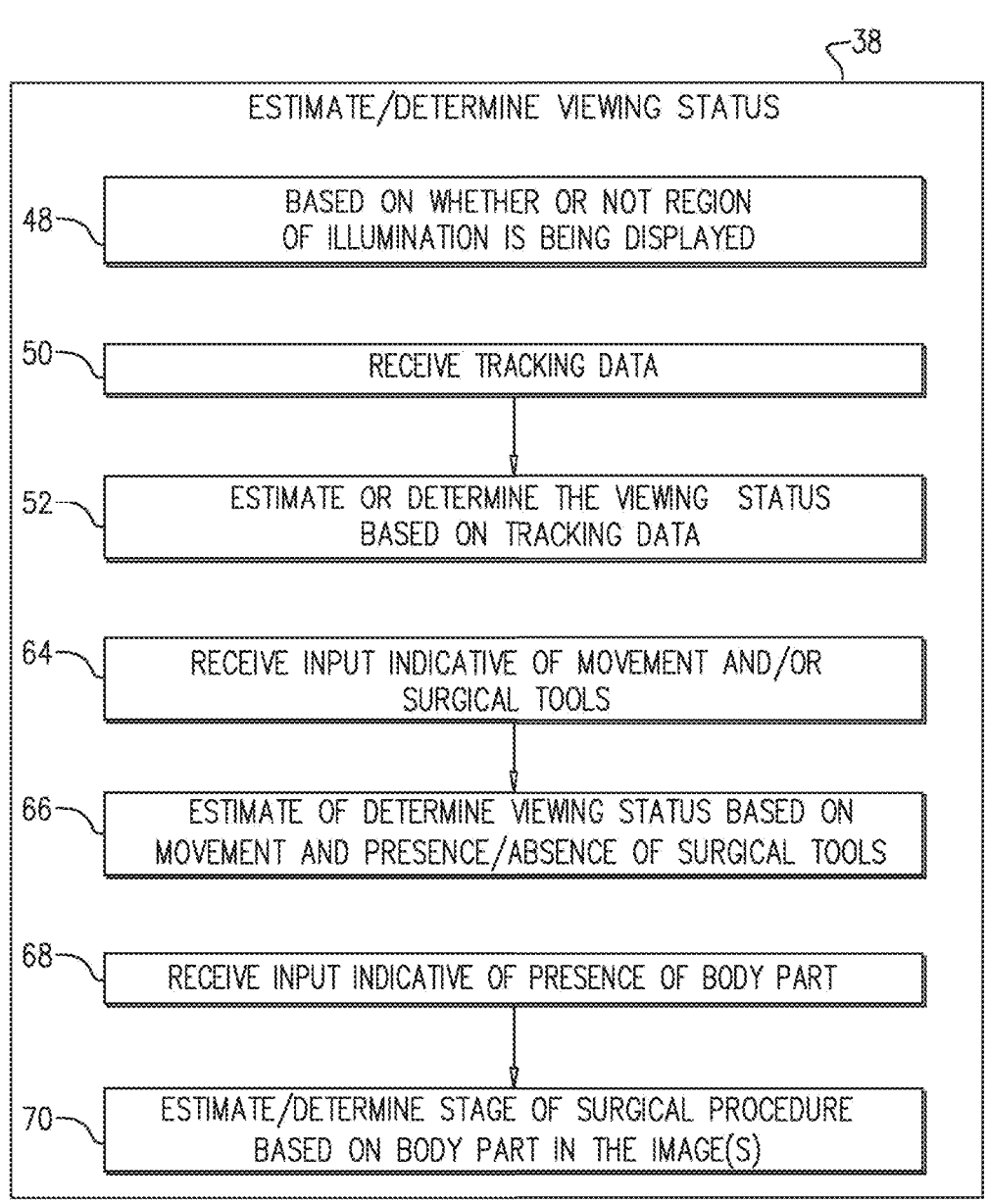
FIG. 4 is a more detailed view of the estimate/determine the viewing status step included in the flowchart of FIG. 2.

Reference is now made to FIG. 4, which is a more detailed view of the estimate/determine the viewing status step of block 38 of FIG. 2. Reference is also made to FIGS. 1a and 1b. The viewing status may be estimated or determined in a variety of ways which may be used independently, or in any suitable combination, to estimate or determine the viewing status. It will be appreciated that other ways for estimating or determining the viewing status may also be used to implement the surgical microscope system 10.

The estimation/determination of the viewing status may be based on any one or more of the following inputs, by way of example only: what the surgeon 30 decides to see via the head-mounted display 32; tracking the orientation and/or the position of the head-mounted display 32 including using a flag for standby indicating when the head-mounted display 32 is not in use; eye-gaze tracking (e.g., via the head-mounted display 32); head and eye tracking via other sensors (e.g., when the head-mounted display 32 is not included in the system 10); and/or data from a proximity sensor which indicates whether someone (e.g., the surgeon 30) is in proximity to an eyepiece(s) through which image data originating from the surgical microscope system 10 can be viewed. The estimation/determination of the viewing status may provide one or more of the following outputs, by way of example only: a probability (e.g., confidence score) that the surgeon 30 is watching the region of illumination (either directly or indirectly); selective data from the inputs, such as position and orientation data, and eye-gaze direction. It should be noted that the outputs may include time stamps so that timings and durations may be used in estimating or determining the lighting need of the surgeon 30. For example, in estimating or determining the lighting need of the surgeon 30, if it may be determined that the head-mounted display 32 is pointing away from the region of illumination and additionally there is no motion in the region of illumination for five consecutive seconds, then a decision may be determined to decrease illumination.

One indication of the viewing status is whether or not the surgeon 30 is watching a screen that includes a live magnified video of the region of illumination. It should be noted that the surgeon 30 may be watching a screen displaying preoperative data that also includes a picture-in-picture (PIP) displaying the live magnified video of the region of illumination. If the surgeon 30 is donning the head-mounted display 32 (which may be indicated by movement of the head-mounted display 32) the viewing status may be estimated or determined by what is being displayed by the head-mounted display 32. If the surgeon 30 is not donning the head-mounted display 32, the surgeon may be viewing the live magnified image via the external display 34 and the viewing status may be estimated or determined by what is being displayed by the external display 34. Therefore, the controller 18 may be configured to estimate or determine the viewing status of the region of illumination based at least on whether or not the region of illumination is being displayed (block 48).

Alternatively, or additionally, the controller 18 may be configured to analyze head or other movements of the surgeon 30 and/or movements of the head-mounted display 32 based on tracker data to determine the viewing status of the magnified image. For example, during rapid head movements or when looking sideways, the controller 18 may assume that the surgeon 30 is not concentrating on the magnified image. Another example is when the surgeon is not donning the head-mounted display 32 which may be detected by lack of movement of the head-mounted display 32 as tracked by a tracker system. It should be noted that during both initial and final stages of the surgical procedure, the surgeon 30 may prefer not to don the head-mounted display 32 since a magnified image may not be used at these stages, yet the illumination is still needed by the surgeon 30. In such a case, motion detected in the region of illumination may indicate that the illumination should be kept unchanged. The tracker system may also detect that the surgeon 30 has stepped away from the region of illumination. The tracker may be based on an optical tracker and or inertial sensors, e.g., accelerometers, or any other suitable tracker.

Alternatively, or additionally, the viewing status may be determined based on given positional or angular boundaries of the head-mounted display 32 outside of which illumination is not required at all or at the current level. The positional and angular boundaries may be user-defined (e.g. surgeon-specific).

Therefore, the controller 18 may be configured to: receive (block 50) tracking data of the surgeon 30 or the head-mounted display 32; and estimate or determine (block 52) the viewing status of the region of illumination based at least on the tracking data. The tracking data may include any one or more of the following: a position of a head of the surgeon 30 and/or the head-mounted display 32; a rate of movement of the head and/or the head-mounted display 32; an orientation of the head and/or the head-mounted display 32; and/or eye gaze data. It should be noted that the system 10 may support multiple users (e.g., 2 or 3 users) and any one of these users may be watching the video of the live magnified image. It should also be noted that other people in the operating room, e.g., a nurse, may be tracked.

The tracking data may indicate that the region of illumination is not being viewed by the surgeon 30 when the tracking data indicates any one or more of the following: head movements greater than a given rate; the surgeon 30 is looking outside (i.e., is not looking in the general direction) of the region of illumination or outside of given angular boundaries (it should be noted that when using a head-mounted display the surgeon may still see the region of illumination and attend to it while pointing the head away from the surgical site. However, when the surgeon is turning the head away from the illuminated region by more than a given threshold it may be assumed that the surgeon is not attending the surgical site); the head-mounted display 32 is not moving as it is not being worn; the head-mounted display 32 is stowed; the surgeon 30 is peeking around the head-mounted display 32 away from the region of illumination; and the surgeon 30 has stepped away from a given region where the surgical procedure is taking place. The tracking data may indicate that the region of illumination is being viewed by the surgeon 30 when the tracking data indicates any one or more of the following: the surgeon 30 is looking towards the region of illumination or inside of the given angular boundaries when the head-mounted display 32 is transparent or in a transparent state (i.e. when the head mounted display can switch between a transparent state as in augmented-reality head mounted systems and an opaque state as in virtual-reality head mounted systems); the surgeon 30 is peeking around the head-mounted display 32 but towards the region of illumination; and the head-mounted display 32 is stowed or is not being worn, but the surgeon 30 is looking at the region of illumination (which may be determined based on an external camera tracking the head of the surgeon 30 or by any other suitable method).

The controller 18 may be configured to: use eye gaze data of the surgeon 30, comprised within the tracking data, indicating where the surgeon is looking within the magnified video of the patient's eye or other body part that is displayed via the head-mounted display 32 (and optionally additional data such as the location of various identified segments in the image, as received from the image analysis block, which enables translating the information of where the surgeon 30 is looking at within the displayed image to a part of the patient's eye that is located at the observed coordinates), and to estimate or determine how to adjust a current illumination provided by the lighting unit. For example, the surgeon 30 may be looking at the eye sclera (which may be determined by identifying the coordinates that the surgeon 30 is looking at and determining that they are within the eye sclera, e.g. using image analysis to identify the specific part of the eye that is located at the observed coordinates). In such a case, the illumination provided through the pupil may be stopped or reduced or changed to a different, less damaging, type of light color, for example, but not limited to, IR illumination.

In addition, the eye gaze data can be used to determine where the surgeon 30 is looking also in cases where the surgeon 30 is not looking at the images displayed on the head-mounted display 32, but peeking outside of the head-mounted display 32. When eye-gaze tracking is implemented via sensors in the head-mounted display 32, the peeking direction is relative to the head-mounted display 32. Since the head-mounted display 32 movements are also tracked, the peeking direction relative to the illuminated region can be determined. For example, the surgeon 30 may be peeking outside the head-mounted display 32, and not at the illuminated region. In such a case, the illumination may be changed (e.g. stopped or reduced).

It is to be noted, for example, that if the system 10 comprises eye-gaze tracking, and an eye-gaze subsystem indicates that the surgeon 30 is focusing on a local saturated part of the magnified image (e.g. found during image analysis), then the system 10 may eliminate the saturation by reducing the illumination globally or locally (using spatial modulation described in more detail below with reference to FIGS. 6 and 7). If the system 10 does not comprise eye-gaze tracking, the image analysis process may further identify a shape in the image as a tool and the system 10 may estimate that the surgeon 30 is focusing on that tool. Alternatively, the system 10 may estimate that when a small area is saturated in a certain stage of the surgical procedure then the illumination may be reduced.

In some cases, the tracking data can include proximity data obtained by a proximity sensor. For example, if the surgical microscope system 10 includes an eyepiece(s) through which the magnified illuminated region can be viewed and a proximity sensor which indicates whether someone (e.g., the surgeon 30) is in proximity to the eyepiece(s), it will be appreciated that a viewing status may be indicated based on whether or not someone (e.g., the surgeon 30) is in proximity to the eyepiece(s). The proximity sensor may be implemented as a camera which detects the head of the surgeon 30 or any other suitable proximity sensor such as a touch sensitive sensor or time-of-flight sensor by way of example only. Therefore, the controller 18 may be configured to: estimate or determine the viewing status of the region of illumination based at least on the proximity data, providing an indication of whether or not the surgeon 30 is in proximity to the eyepiece(s) of the surgical microscope system 10.

The viewing status of the region of illumination by the surgeon 30 may be indicated by at least movement in, or generally around, the region of illumination or the presence/absence of tools in, and generally around, the region of illumination. Movement is typically determined based on results of image analysis processing. The image analysis processing may comprise any suitable method or methods, for example, but not limited to, using motion detection algorithm as a part of the image analysis along with one or more other image processing techniques.

It will be appreciated that the viewing status may be based on any suitable combination of factors described herein. The movement or the tools may be detected based on image analysis of the magnified image. When no movement and/or no tools are detected, the illumination may be reduced or stopped. When a tool or movement is again detected in, and generally around, the region of illumination, the illumination may be increased. The tools may be moved manually or mechanically or even as part of a robotic surgery system. Therefore, the controller 18 is configured to: receive input (block 64) indicative of movement and/or surgical tools at least at the region of illumination; and estimate or determine (block 66) the viewing status of the region of illumination based at least on the movement, and/or a presence or an absence of the surgical tools in at least the region of illumination. It should be noted that the movement detection is not restricted to the region of illumination, but may also include an area around the region of illumination. Motion/movement detection and tool detection may be performed based on a low-resolution video taken by a camera either disposed in or adjacent to the surgical microscope system 10, or based on video taken by microscope system 10 itself.

It should be noted that very high-resolution cameras may be used for imaging a relatively large field of view (FOV), and the user or surgeon 30 may choose to zoom in to see only a small part of the FOV (hence the FOV image is magnified). Although the surgeon 30 sees a part of the FOV, the entire FOV is still generally imaged. Motion detection may be based on the full image (either the original image or a binned image (an image having a smaller resolution than the full image but covering the entire FOV derived from the original image). It should also be noted that motion detection may be based on video from one of the microscope cameras or even based on video from more than one camera as previously mentioned above.

Employing motion and/or tool detection generally uses some sort of illumination in, and generally around, the region of illumination. Therefore, completely shutting down the illumination in periods when no motion or tools are detected is generally not appropriate. A lower level or pulsed illumination may be used. Alternatively, IR illumination may be used for motion detection instead of using white light illumination. It should be noted that if a camera that is used for generating the magnified image (and is focused for white light) is also used for motion detection with IR light, then the IR video might be out of focus (depending on the camera optics), but motion detection may generally still be performed.

Similarly, the controller 18 may be configured to: receive input (block 68) indicative of whether a body part that is being operated on is included in the image(s); and estimate or determine (block 70) the viewing status based at least on whether the body part is included in the image(s).

It should be noted that tool detection and other image analysis functions may also be used to estimate the stage of the surgical procedure. Therefore image analysis, in addition, or alternatively, to providing a direct estimation or determination method of the illumination needs of the surgeon 30, and in addition, or alternatively, to providing input to estimate or determine the viewing status, also provides an input to estimating or determining the stage of the surgical procedure. If the stage estimation/determination is implemented using machine learning, image analysis may be used during both the learning phase and the operation phase. Additionally, or alternatively, data used and/or outputted in determining/estimating the viewing status may be used to estimate the stage of the surgical procedure.

Figure 5:
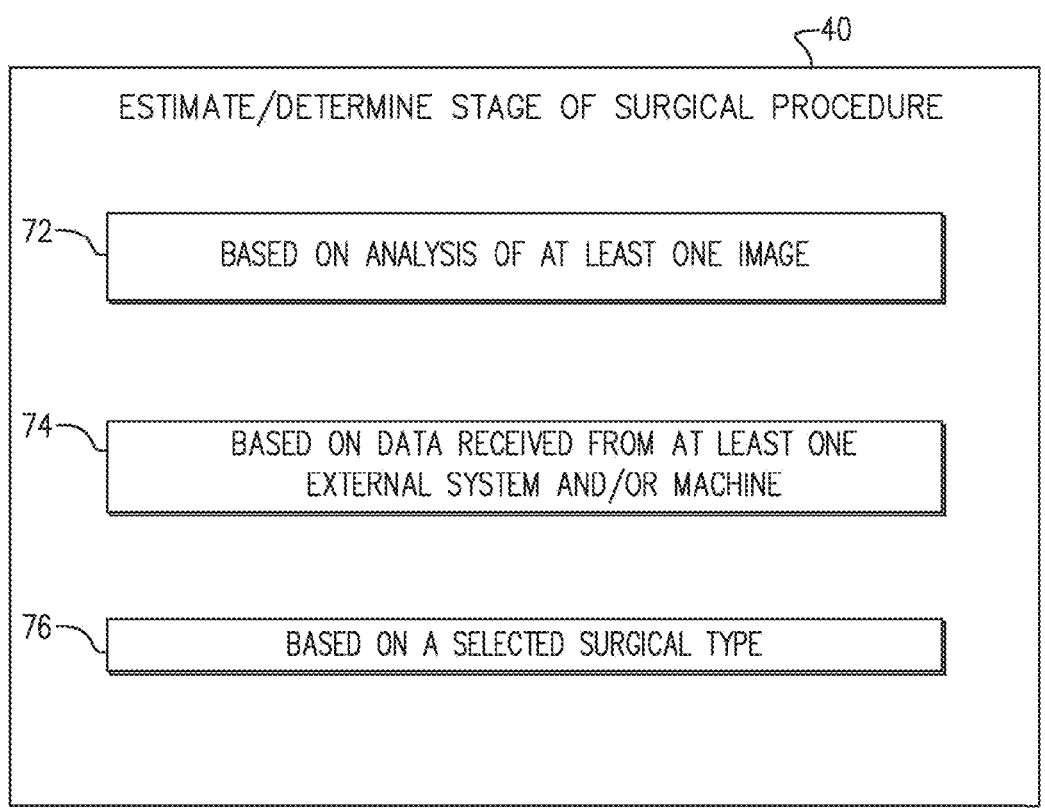
FIG. 5 is a more detailed view of the estimate/determine the stage of surgical procedure step included in the flowchart of FIG. 2.

Reference is now made to FIG. 5, which is a more detailed view of the estimate/determine the stage of surgical procedure step of block 40 of FIG. 2. Reference is also made to FIGS. 1a and 1b.

In eye surgery, by way of example, there are stages during surgery when the surgeon is focused on surgical locations in which illumination through the pupil is not required. Examples for such periods are when the surgeon places trocars in the eye sclera at the beginning of a vitreoretinal surgery, and when the surgeon removes the trocars and stitches the sclera at the final stages of the surgery.

By way of another example, in vitreoretinal surgery the majority of the procedure is performed with fiber illumination that is not controlled by the surgical microscope system 10, and the surgical microscope system's 10 illumination is turned off. The controller 18 can be configured to identify the stage of the procedure as a posterior-eye stage based on various indication/s (e.g. the user switches to posterior-eye mode, the automatic detection of lowering an arm holding a noncontact lens by the surgeon, and/or other system characteristics are changed in a manner that is specific for a posterior-eye procedure) and turn off the illumination automatically.

By way of another example, in anterior-segment procedures various stages of the procedure require coaxial illumination for generating red reflex from the retina. The controller 18 can be configured to identify the stage of the procedure as a stage requiring coaxial illumination based on various indications, and adjust the flood and coaxial illuminations respectively and per the predetermined settings of the surgeon 30.

It will be appreciated that in other non-eye surgical procedures, such as brain surgery, similar consideration may also be relevant in that certain stages of surgery use a spectrum and intensity of illumination, whereas other stages may use a different spectrum and/or intensity of illumination or no illumination.

The estimation/determination of the stage of surgical procedure may be based on any one or more of the following inputs, by way of example only: a procedure type that was selected via a user interface (e.g., a touchscreen); data from external machines/systems (e.g. a Phaco machine) or the existence of an active connection with given external machines/systems; data indicating movement of a camera-head unit 35; if the camera-head unit 35 or an arm holding it include motors to control focus, x-y movement, etc. then data from at least one controller of the motors; if the camera-head unit 35 is suspended by a robotic arm then data from a controller of the robotic arm; if the camera-head unit 35 is suspended by a manual arm then data from accelerometers in camera-head unit 35; and/or data available in "viewing status" and "image analysis" processes. The output(s) may then be used along with a recommended illumination for each stage (which may be user-specific) in estimating or determining the lighting need of the surgeon 30. It should also be noted that "stage estimation" may be personalized since each surgeon may perform specific stages in a surgical procedure and have different habits during the various stages, therefore estimation/determination of the stage of surgical procedure may also be based on surgeon identity.

The controller 18 can be configured to estimate or determine the stage of the surgical procedure based at least on analysis of at least one image captured by the surgical microscope system 10 (block 72). For example, image analysis can be used to determine whether a body part is included in the image(s), and the stage of the surgical procedure can be estimated or determined based at least on whether the body part is included in the at least one image. By way of another example, image analysis can be used to determine whether a specific tool in the image(s), and the stage of the surgical procedure can be estimated or determined based at least on whether the tool is included in the at least one image.

Alternatively, or additionally, the controller 18 is configured to estimate or determine the stage of the surgical procedure based at least on data received from at least one system or machine disposed externally to the surgical microscope system 10 (block 74).

Alternatively, or additionally, the controller 18 is configured to estimate or determine the stage of the surgical procedure based at least on a selected surgical procedure type (block 76).

Machine learning may be employed to automatically identify the various surgical procedures and the various stages in each procedure in which illumination is, or is not, used by the surgeon 30. The machine learning may even determine how different stages need different illumination levels, or different spectra of illumination and which parts of the body are illuminated (e.g., pupil versus the rest of the eye). This may be performed using supervised and/or unsupervised learning, using time-segmented and tagged video recordings, and/or raw footage in procedures where the surgeon 30 (or other surgeon) manually changes the illumination according to the lighting needs during the surgical procedure, or any other suitable method. The machine learning may be additionally based on one of: raw video data from cameras generating magnified images; raw video from other cameras (e.g. an IR camera having a larger field of view); output of image analysis algorithms performed on that raw video (e.g., algorithms that identify tools in the image; other data such as data from external machines/systems or tools (e.g. a phacoemulsification machine, a phacovitrectomy system, etc.) that are connected to the surgical microscope system 10 for displaying various data to the surgeon 30 via the head-mounted display 32 and/or the external display 34; or the existence of an active connection with a given external machines/systems; and/or a user input that selects a procedure type via a graphic or other user interface system of the surgical microscope system 10; and/or the identity of the surgeon 30.

It will be appreciated that neural networks and the like may not be organized in blocks, such as the blocks included in FIGS. 2-5, and if the stage estimation/determination or other estimation/determination described herein, such as an estimated/determined current required illumination, is implemented using machine learning then the neural network may be represented by a black box receiving many inputs, and generating an output representing the estimated/determined stage, or the estimated/determined current required illumination respectively. Therefore, it will be appreciated that the blocks of FIGS. 2-5 are only for the sake of simplifying the understanding of the method and are not intended to limit the scope of the method. The steps may be performed in any order, simultaneously or in a black box type environment as described above.

Figure 6A:
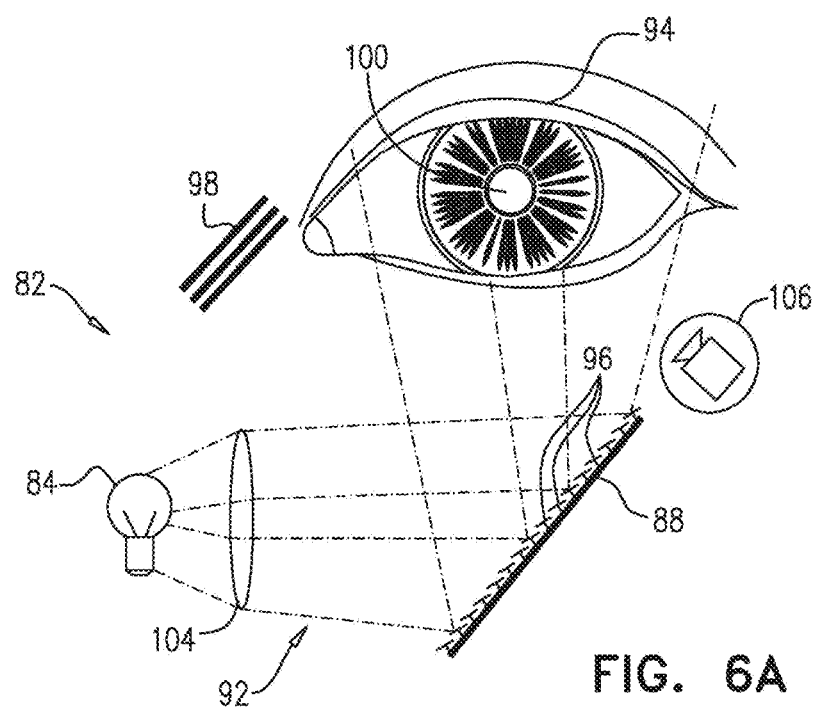
FIGS. 6a and 6b are partly pictorial, partly block diagram views of a dynamic light masking device configured to modify a spatial pattern of illumination from a single light source for use in the surgical microscope system of FIGS. 1a and 1b.
Figure 6B:
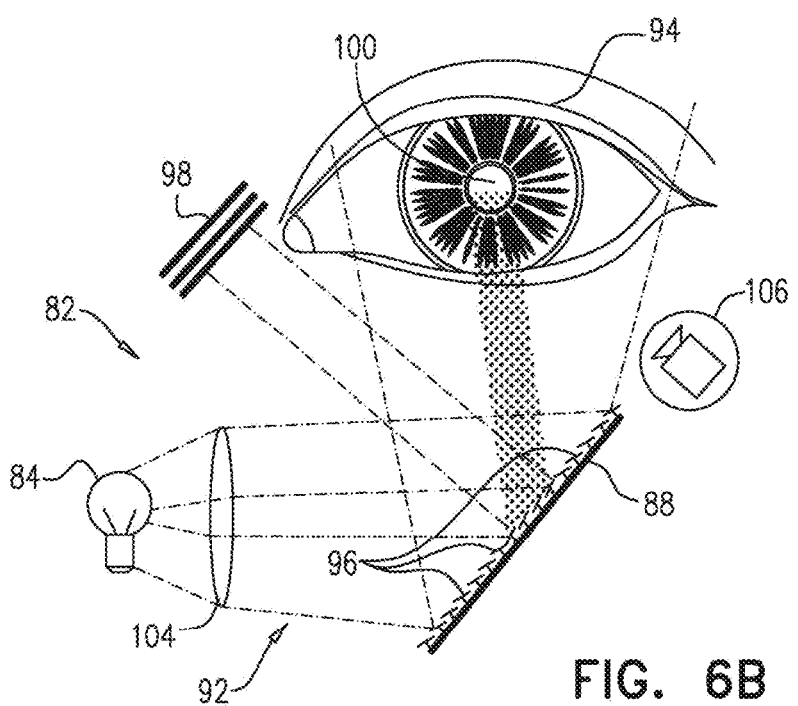

Reference is now made to FIGS. 6a and 6b, which are partly pictorial, partly block diagram views of a dynamic light masking device 82 configured to modify a spatial pattern of illumination from a single light source 84 for use in the surgical microscope system 10 of FIGS. 1a and 1b. Reference is also made to FIGS. 1a and 1b.

The adjustment to the illumination may include starting, stopping, dimming, increasing, or otherwise changing the illumination provided by the lighting unit 14. "Otherwise changing the illumination" includes changing a spatial and/or temporal pattern of the illumination. The various adjustments to the illumination are now described in more detail.

The lighting control system 12 may be configured to dim the illumination using any one or more of the following: (a) changing the temporal radiation pattern of the lighting unit 14 to a pulsing radiation pattern rather than a continuous one, thus reducing the total irradiation power; (b) electrically controlling a permanent liquid crystal shutter (LCS) disposed in an optical path of the lighting unit 14 wherein the opacity of the LCS and thus the illumination intensity may be controlled electronically; (c) automatically disposing a beam splitter into the optical path; and (d) automatically disposing a neutral-density filter into the optical path.

The adjustment to the illumination may include changing a spectrum of radiation of the illumination provided by the lighting unit 14, wherein the spectral power of the illumination may be modified in order to reduce the portion of the hazardous blue light within that illumination. An optical element that blocks the blue light may be automatically inserted in the optical path of the illuminating light (e.g. a long-pass optical filter or a dichroic mirror). Alternatively, or additionally, the lighting unit 14 may include two or more light sources, where the spectrum of one of the sources is less hazardous than of the other. The lighting unit 14 may be configured to automatically alternate between the sources in order to achieve momentarily reduction of hazardous light illumination (for instance the alternative light source could be in the near IR region, since imaging sensors usually operate in wavelengths up to 1050 nm). Therefore, the lighting unit 14 may be configured to change the spectrum of radiation of the illumination from a more harmful spectrum of radiation such as white light to a less harmful spectrum, such as IR light, that does not contain a harmful component, using any one or more of the following: disposing one or more optical components between the illumination source and the patient (e.g. a long-pass filter; a dichroic mirror; or a band-pass filter); switching between two or more sources of illumination (e.g., LEDs) having different radiation spectra (an example of this is described with reference to FIGS. 7a and 7b) and/or different radiation directions (i.e. flood vs. coaxial); or any other suitable optical arrangement.

Coaxial illumination may be based on IR light instead of visible light. In such a case image processing may be used to identify the pupil in the IR camera image and to artificially tint the illuminated area within the pupil with red color, so it appears to the surgeon as the standard red reflex and not monochromatic. The system may combine (or fuse) a color image (e.g. using visible flood light) with the IR image (using coaxial IR light) and display the red-tinted IR image inside the pupil and the color image outside the pupil. If the surgeon so desires, the system may similarly transform the colors of all or a portion of the image to any color that the surgeon may desire. For example, they may prefer a purple reflex or a green reflex rather than the standard red reflex.

Reducing the damaging illumination may be based on dynamically blocking only the light that illuminates the retina (or other sensitive body part), in the periods of time when it is not required for the surgical procedure. Therefore, the adjustment to the illumination provided by the lighting unit 14 may include modifying a spatial pattern of the illumination. Modifying the spatial pattern of the illumination may include dimming or stopping illumination of a first part of the region of illumination, or of a body part therein, while leaving the illumination of a second part of the region of illumination, or of the body part therein, unchanged. The lighting unit 14 may include the dynamic light masking device 82 configured to modify the spatial pattern of the illumination for example by modifying the illumination pattern that is reflected off the surface of the dynamic light masking device 82 or that is transferred through the dynamic light masking device 82. The dynamic light masking device 82 may include any one or more of the following to at least partially modify the pattern of illumination: a digital mirror device 88 shown in FIGS. 6a and 6b; a digital mirror device in an optical path of two radiation sources to selectively select between the two radiation sources shown in FIGS. 7a and 7b; a spatial light modulator; a movable spatial filter or mask or mirror or lens; and a liquid crystal shutter.

The use of the digital mirror device 88 is now described in more detail with reference to FIGS. 6a and 6b. The digital mirror device 88 is disposed in a path of a light beam 92 generated by the light source 84 that illuminates an eye 94 during the surgical procedure. The light beam 92 may be modified by a suitable configured lens 104. The digital mirror device 88 includes a plurality of computer controlled micro-mirrors 96 (only some are labeled for the sake of simplicity) which may be controlled by the controller 18 or any suitable processing resource. At least some of the micro-mirrors 96 may be in one of two angular positions or states. One is considered an 'ON' state, in which light that impinges on the micro-mirror 96 is reflected towards a pupil 100 of the eye 94 as shown in FIG. 6a. The other is considered an 'OFF' state in which light that impinges on the micro-mirrors 96 is reflected away from the pupil 100 and towards an optional beam blocker 98 as shown in FIG. 6b. The micro-mirrors 96 may support a spectrum of angular states but the above two states of the various states are used herein. The ON and OFF angles of each micro-mirrors 96 may be re-calibrated periodically or for each surgical procedure. A digital camera 106 may be configured to continuously or periodically capture a video of the eye 94 and transfer the data to the controller 18. The controller 18 analyzes the image(s) using an image processing algorithm and determines the location, size, and shape of the pupil 100 relative to the illuminated area. Using this information the controller 18 may configure the digital mirror device 88 to locally turn off the light that impinges on the pupil 100 by controlling the state of each micro-mirror 96 in the digital mirror device 88. Thus, the computer can dynamically control the illumination pattern that is illuminated onto the eye 94.

The determination of which of the micro-mirrors 96 are illuminating which areas in the surgical field may be accomplished in different ways. One method is to switch different groups of the micro-mirrors 96 on and off and analyze the image taken by the digital camera 106. Another method is based on pre-calibration of the position and orientation of the digital camera 106 relative to the digital mirror device 88. It should be noted that in the second method, depth information may also be used and may be retrieved by using two calibrated cameras or a 3D sensor by way of example only.

Figure 7A:
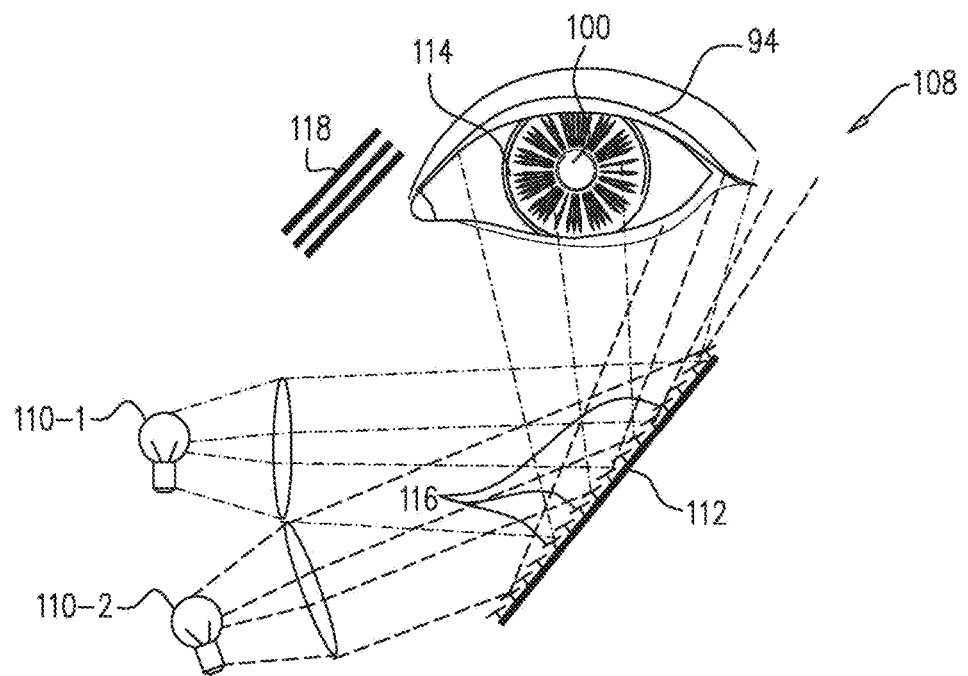
FIGS. 7a and 7b are partly pictorial, partly block diagram views of a dynamic light masking device configured to modify a spatial pattern of illumination from two different light sources for use in the surgical microscope system of FIGS. 1a and 1b.
Figure 7B:
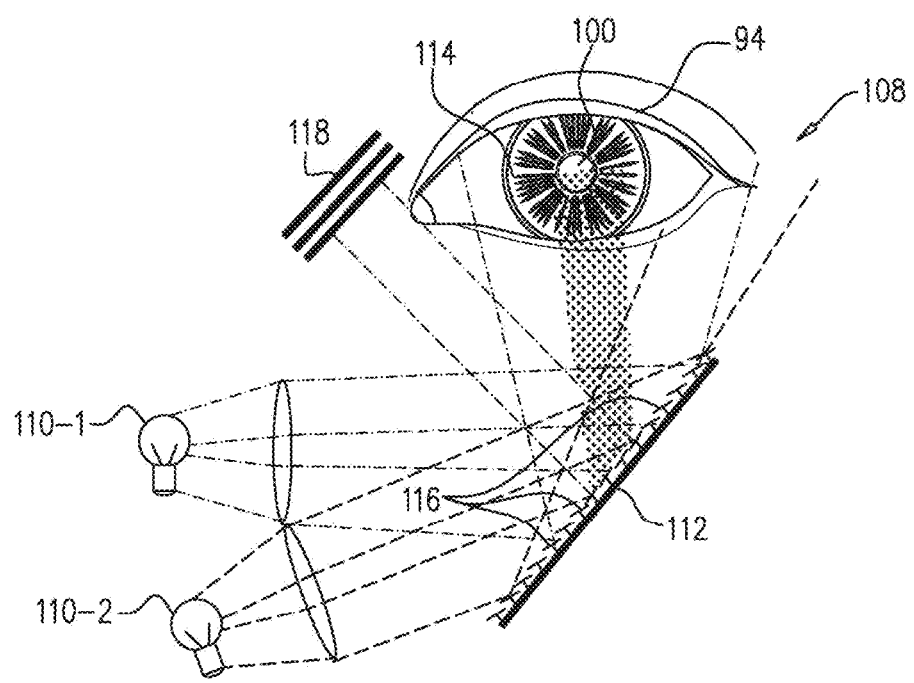

Reference is now made to FIGS. 7a and 7b, which are partly pictorial, partly block diagram views of a dynamic light masking device 108 configured to modify a spatial pattern of illumination from two different light sources 110 for use in the surgical microscope system 10 of FIGS. 1a and 1b. Reference is also made to FIGS. 1a and 1b. FIGS. 7a and 7b illustrate modifying the spatial pattern of the illumination by changing a radiation spectrum incident on a first part (e.g., the pupil 100) of the region of illumination, or of a body part therein (the eye 94), while leaving the radiation spectrum incident on a second part (e.g., the rest of the eye 94) of the region of illumination, or the body part therein, unchanged. The dynamic light masking device 108 may include a digital mirror device 112 in an optical path of the two radiation sources 110 to selectively select between the two radiation sources 110.

One of the light sources 110 may be a white light source 110-1 that is more hazardous to the eye 94, and the other light source 110 may be a less harmful light source 110-2. The less harmful light source 110-2 can be either a visible or an IR light source. The digital mirror device 112 may include two states, a state S1 and a state S2. In state S1, shown in FIG. 7a the pupil 100 and an iris 114 are both illuminated by the white light source 110-1. In state S2, shown in FIG. 7b, the pupil 100 is illuminated by the less harmful light source 110-2 and the iris 114 by the white light source 110-1 while some of the white light is reflected away from the eye in the direction of a beam blocker 118. The digital mirror device 112 includes a plurality of micro-mirrors 116 (only some labeled for the sake of simplicity) which may be individually controlled by the controller 18 to selectively generate state S1 or state S2.

The controller 18 may be configured to selectively change states from S1 to S2 to provide spatial pattern modification and optionally temporal pattern modification. For example, the controller 18 may be configured to illuminate the retina with white light once every several imaging cycles and with less harmful light during the rest of the imaging cycles (i.e. temporal modulation). In this way, continuous imaging of the retina may be achieved, but the overall light hazard is reduced. By way of an additional example, the controller 18 may be configured to select state S1 when the surgeon 30 is looking at the retina or the pupil 100 or has tools in the pupil 100 region and select state S2 at other times.

It should be noted that the use of IR or other non-visible light assumes that the surgeon 30 is watching a digital image of the surgical field either using the head-mounted display 32 or the external display 34. Using an IR light source is generally not used when the surgeon 30 is looking directly at the surgical field, with or without optics. Similarly, the IR light may be incorporated in a diagnostic microscope known commonly as a slit lamp microscope for performing eye exams. IR light in a slit lamp microscope will provide the advantage of a more pleasant experience for the patient and brighter, better defined images of the anatomy for the eye doctor.

It should also be noted that the dynamic light masking device 82 of FIGS. 6a and 6b and the dynamic light masking device 86 may also enable illuminating various regions of the surgical field with various intensities. This may allow achieving an image with a better dynamic range, i.e., reducing saturation in bright areas of the image while imaging dark areas with high detail. A computer algorithm may be used to find saturated areas in the image. Saturated areas often occur because the irradiation power that is required to image the region of illumination is such that other areas in the image that might be bright or highly reflective saturate. The algorithm may locally eliminate the local saturations by projecting an uneven illumination across the image.

Figure 8:
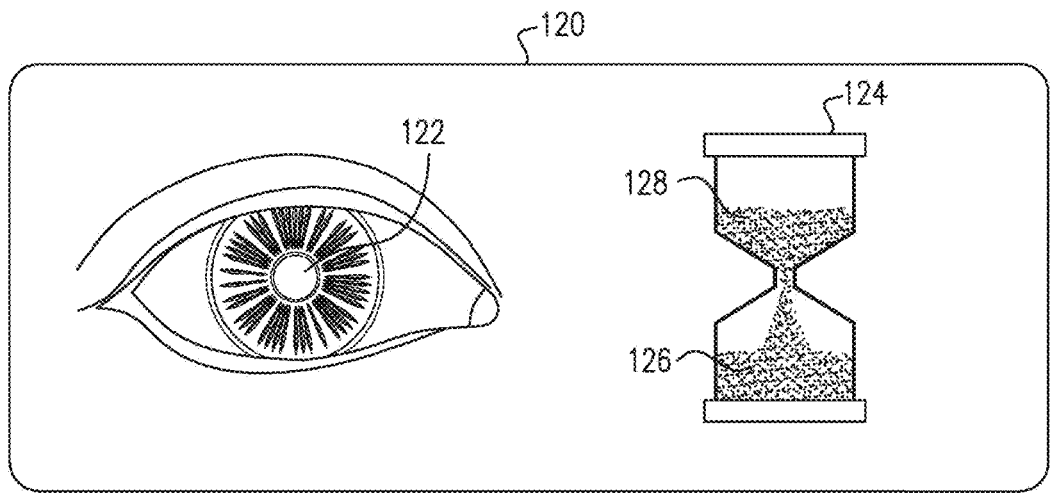
FIG. 8 is a pictorial view of a display showing a body part and an indication of an amount of radiation that has entered the body part for use with the surgical microscope system of FIGS. 1a and 1b.

Reference is now made to FIG. 8, which is a pictorial view of a display 120 showing a body part 122 and an indication 124 of an amount of radiation that has been irradiated on the body part for use with the surgical microscope system 10 of FIGS. 1a and 1b. Reference is also made to FIGS. 1a and 1b. The surgical microscope system 10 may be configured to continuously detect whether light was irradiated on the body part 122 (e.g., a patient's pupil) and monitor the illumination levels during these periods of time. Indications of the accumulated levels of weighted harmful light exposure may be brought to the attention of the surgeon 30 via the indication 124 which may also indicate a limit of allowed or recommended radiation in accordance with a standard. A software application may calculate accumulated harmful light exposure to a certain body part. The software application may take into account the exact time periods when the body part is illuminated, and the illumination power in each period. The software application may take into account the spectrum of each light source using a spectral weighted function to accurately accumulate the harmful light portion of each light source. Weighted spectral function is described, for example, in regulatory documents such as ANSI Z80.36-2016. The software application may analyze the real-time image of the eye to determine what portion of the illumination incident on the eye is incident on the retina. For example, the software application may take into account the size of the pupil and the opacity of the eye. It should be noted that phototoxicity damage during ophthalmic surgery occurs mostly in retinal cells. As described above, light can harm the body in various ways, for example, but not limited to, by thermal heating. Alternatively, or additionally, exposure to thermal heating due to illumination may also be determined and indicated by the surgical microscope system 10. For example, the hour-glass indicator 124 shown in FIG. 8 may indicate a cumulative light exposure (by a shading 126 in the bottom of the hour-glass) and a remaining allowed exposure (by a shading 128 in the top of the hour-glass). It will be appreciated that the display 120 may include more than one indicator 124 indicating light exposure compared to a standard for one or more different radiation spectra. The indicator(s) 124 may be disposed on any part of the display 120 and using any suitable format. The display 120 may be part of the head-mounted display 32 or the external display 34, by way of example only.

Figure 9:
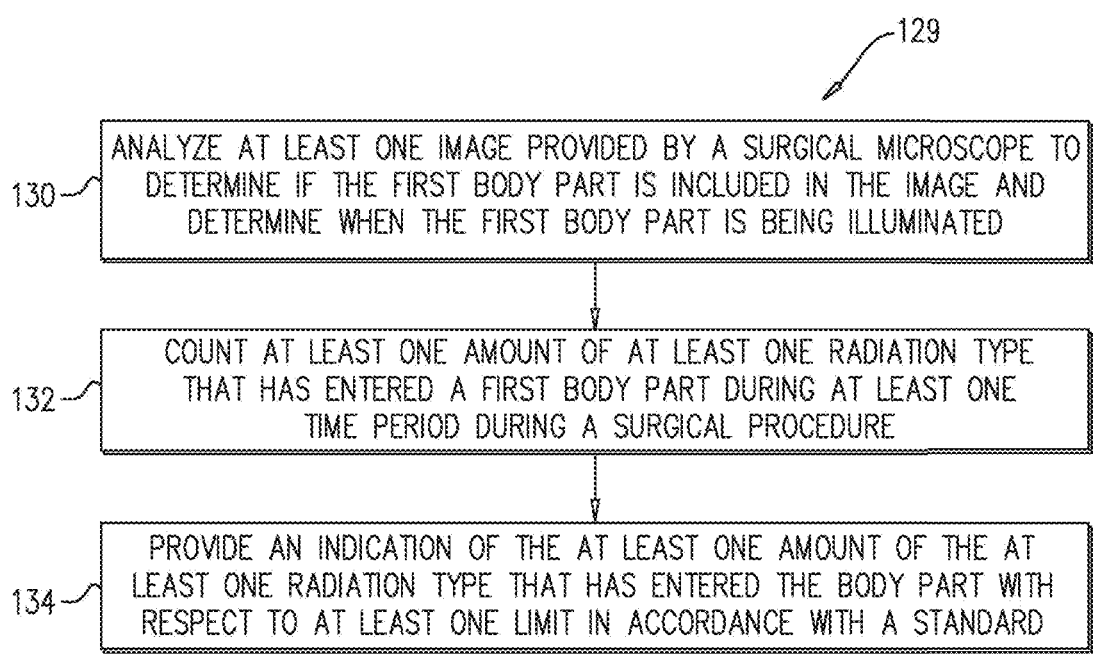
FIG. 9 is a flowchart including exemplary steps in a method of monitoring an amount of radiation that has entered a body part for use with the surgical microscope system of FIGS. 1a and 1b.

Reference is now made to FIG. 9, which is a flowchart 129 including exemplary steps in a method of monitoring an amount of radiated energy that has entered the body part 122 for use with the surgical microscope system 10 of FIGS. 1a and 1b. Reference is also made to FIGS. 1a and 1b. The controller 18 may be configured to analyze (block 130) at least one image provided by the surgical microscope system 10 to determine if the body part 122 is included in the image and determine when the body part 122 is being illuminated. The counter 22 may be configured to count (block 132) at least one amount of at least one radiation spectrum that has irradiate the body part 122 during at least one time period during the surgical procedure. The controller 18 may be configured to provide (block 134), to an output or storage device (e.g., the head-mounted display 32, the external display 34, hard-drive, etc.) the indication 124 of the at least one amount of the at least one radiation spectrum that has entered the body part 122 during the at least one time period with respect to at least one limit of allowed radiation in accordance with a standard. The indication 124 may include any one or more of the following: a recorded message; an audible indication; a textual and/or numeric and/or symbolic indicator (such as an hour glass indicator, a bar level indicator, etc.) displayed in the head-mounted display, or on any other display (e.g. monitor 34).

When the amount of radiation approaches its limit, the surgical microscope system 10 may automatically reduce, or offer the surgeon to manually reduce, the illumination and work with degraded performance. The surgical microscope system 10 may perform one or more compensatory actions to retain image brightness while degrading other image characteristics such as: opening a shutter of the image capture unit 16 allowing a reduction in the illumination but degrading the depth of field; increasing a sensor integration time of the image capture unit 16 which reduces the frame rate leading to a smearing of moving elements in the image; Using less harmful light, optionally while compromising the quality of the colors in the captured image; alternating between white light and less harmful light (e.g., IR light) where color compensation may be made to the frames captured with less harmful light using white-light-captured frames; changing the radiation spectrum by using a filter or changing the light source or any other suitable method; and increasing a sensor gain of the image capture unit 16 elevating noise levels in the image (e.g., snow-like effects). Therefore, in response to determining the adjustment to the illumination provided by the lighting unit 14, the controller 18 may be configured to send a signal to the image capture unit 16 to compensate for the adjustment by any one or more of the following: adjusting an opening of the shutter of the image capture unit 16; increasing an integration time of the sensor of the image capture unit 16; using a color correction module to compensate for color loss; and/or increasing a gain of the sensor.

Figure 10:
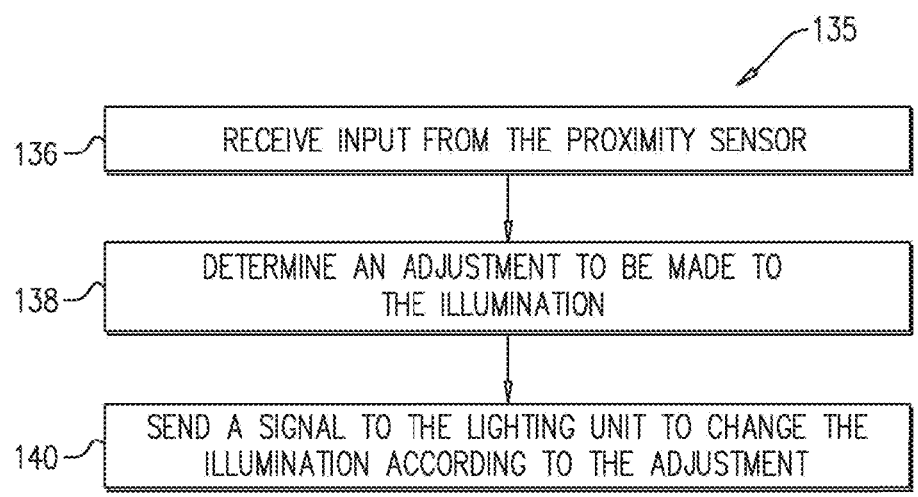
FIG. 10 is a flowchart including exemplary steps in another method of operation of the surgical microscope system of FIGS. 1a and 1b.

Reference is now made to FIG. 10, which is a flowchart 135 including exemplary steps in another method of operation of the surgical microscope system 10 of FIGS. 1a and 1b. Reference is also made to FIGS. 1a and 1b. The controller 18 may be configured to receive (block 136) input from a proximity sensor. The input provides an indication of whether or not the surgeon 30 is in proximity to an eyepiece(s) through which image data originating from the surgical microscope system 10 can be viewed. The controller 18 (FIGS. 1a and 1b) may be configured to determine (block 138) an adjustment to be made to the illumination provided by the lighting unit 14 based on whether or not the surgeon 30 is in proximity to the eyepiece(s). The controller 18 (FIGS. 1a and 1b) may be configured, in response to determining the adjustment, to send (block 140) a signal to the lighting unit 14 to change the illumination according to the adjustment.

It is to be noted that although reference is made herein to a optical and/or a proximity sensor, other/additional sensors can be used to determine whether or not the surgeon 30 is in proximity to an eyepiece(s) through which image data originating from the surgical microscope system 10 can be viewed. For example, a touch sensor can be used, by placing it at a position on the eyepiece so that when the surgeon 30 is viewing the image data therethrough, the surgeon touches the touch sensor. Another example is using a camera(s) to monitor the position of the surgeon's 30 head and using image analysis to determine if the surgeon is looking through the eyepiece.

As mentioned above, using IR illumination of an eye body part may dramatically improve visibility of one or more interior parts of the eye since the IR illumination reaches and is better reflected from the retina.

According to some aspects of disclosed embodiments, there is provided a system for imaging a body part during a medical procedure.

According to some embodiments, the system may include at least:
  at least one image capture unit for imaging the body part, the at least one image capture unit being configured to sense light at least in the infrared (IR) spectrum; an.
  at least one IR light source for illuminating a portion of the body part with light in the IR spectrum, wherein IR light emitted by at least one of the at least one IR light source is coaxial with an optical axis of one of the at least one image capture unit, According to some embodiments, the system may be configured to output imagery data emanating from the at least one image capture unit for displaying thereof.

According to some embodiments, the system may be embedded in or serving as one of: (i) a mono or a stereoscopic surgical microscope, (ii) a diagnostic microscope, (ii) a slit lamp microscope, (iii) an exoscope, (iv) a control interface of a robotic surgery system, and/or (v) a traditional optical microscope with optical eyepieces. According to other embodiments, the system may be external to an optical microscope serving as an auxiliary system to that microscope.

Figure 14:
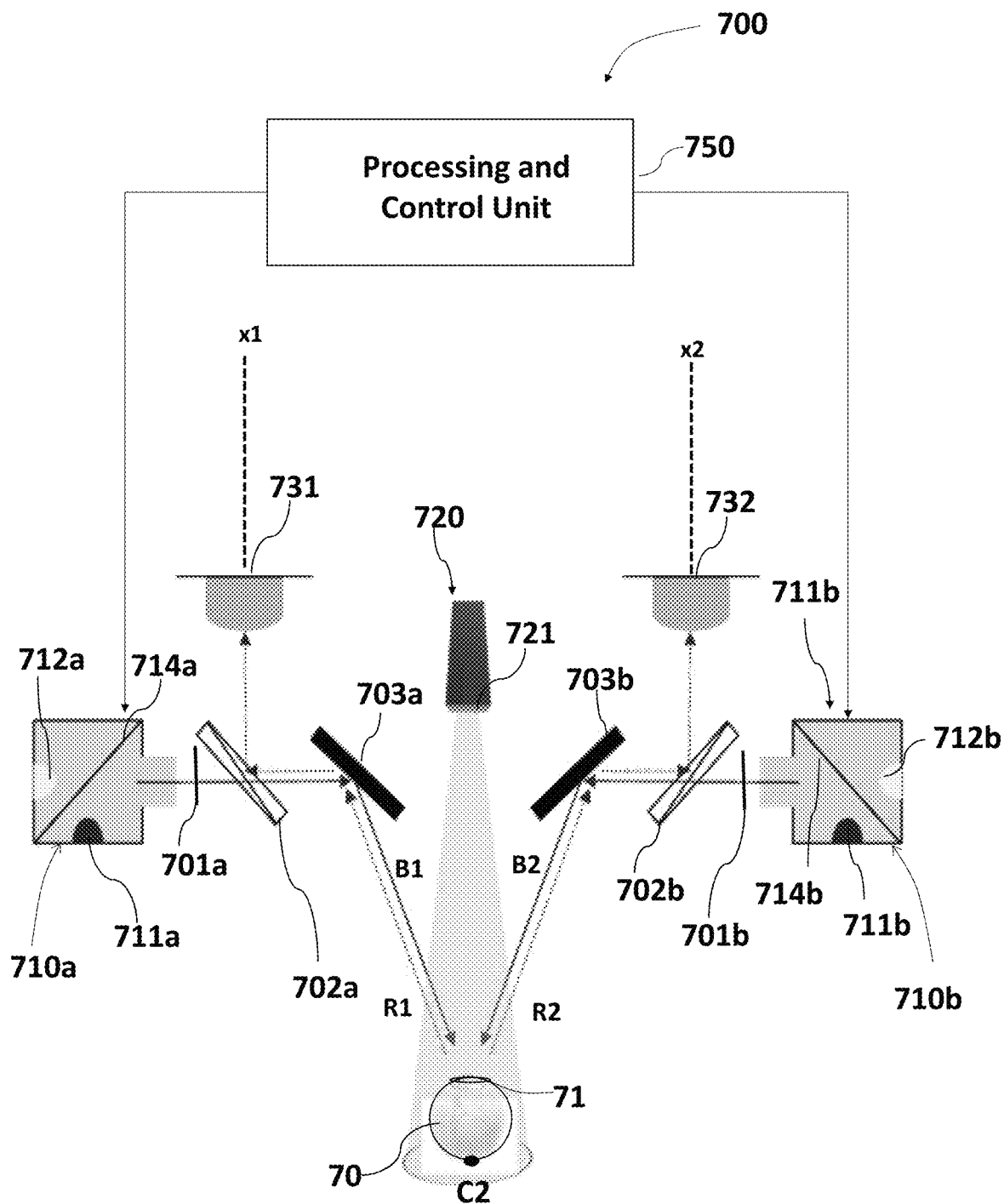
FIG. 14 is a schematic illustration of a system for illuminating of a body part during a medical procedure, using multiple IR and visible light sensing image capture units, according to some embodiments.

In some embodiments, coaxial illumination can be illumination in which light from a light source and/or an optical axis of a camera are diverted by a semi-transparent mirror (e.g., beam splitter) so that the light is projected along an optical axis of the camera. In these embodiments, the light becomes coaxial with the optical axis of the camera only after passing through beam splitter. The terms "coaxial light", "coaxial light source" and "coaxial illumination" are meant to refer to light emitted by a light source that is coaxial with a camera (or viewer in general) at least in part of its optical pathway, and specifically the part in which the light reaches its target (e.g., the body part). These embodiments are illustrated in FIG. 14, in which the light emitted by illumination units 710a and 710b becomes coaxial with the optical axes of cameras 731 and 732 only after passing through beam splitters 702a and 702b. In other embodiments, light emitted by a light source can be coaxial with a camera in its entire optical pathway, for instance when the image capture unit comprises an integrated light source.

In some embodiments, imagery data emanating from the at least one image capture unit is output for display without any processing. In some embodiments, imagery data emanating from the at least one image capture unit is output after being processed. Processing may include, for example, performing debayering, histogram equalization, sharpening, color correction, and the like. In some embodiments, the processing may increase the resolution, the contrast, or the gamma curve of the image. In some embodiments, processing may include cropping a region of interest from an image or images of the imagery data for outputting for display only the cropped region (e.g., as in the case of digital magnification). In some embodiments, processing may include overlaying textual or pictural information on the imagery data. In some embodiments, processing may include overlaying the imagery data as an overlay (for example, as a picture-in-picture) over other images (e.g., video sources internal or external to the system). In all the above embodiments, the processing can be considered as altering the displayable appearance of one or more images or regions of the images of the imagery data.

In some embodiments, the system may also include at least one visible light source for illuminating the body part with light in the visible spectrum.

In some embodiments, at least one of the at least one visible light source may be coaxial with the optical axis of the at least one image capture unit. In some embodiments, at least one of the at least one visible light source may be a flood light.

In the embodiments in which the system includes at least one visible light source, the at least one image capture unit may comprise any combination of one or more image capture units configured to detect light both within the visible spectral range and the IR spectral range. For example, the at least one image capture unit can comprise a single sensor that is capable of sensing light both in visible spectral range and the IR spectral range (such as, for example, an RGB CMOS sensor or an RGB-IR CMOS sensor). As another example, the at least one image capture unit can comprise one sensor for sensing visible light and another sensor for sensing IR light. As yet another example, the at least one image capture unit can comprise several sensors for sensing several spectral ranges (e.g., colors), such as separate sensors for each of the red, green, blue and IR ranges.

In some embodiments, the system may be further configured to enable manual and/or automatic balancing between visible illumination from the at least one visible light source and IR illumination from the at least one IR light source, at least by controlling the intensity of at least one of the at least one visible light source and at least one of the at least one IR light source.

In cases in which the system enables manual balancing of one or more of the light sources, the system may be configured to enable the adjustment of the balance between the illuminations via a user interface. In some embodiments, the imagery data may be processed (e.g., by using one or more processors or processing units including hardware and/or software means to perform the actual processing) to alter the displayable appearance of one or more images of the imagery data e.g., by using one or more image processing algorithms and/or processing hardware and optionally also by using one or more machine learning techniques and/or models.

In some embodiments, the at least one image capture unit comprises at least two image capture units for stereoscopic imaging. In these embodiments, the at least one IR light source can comprise at least two IR light sources, wherein IR light emitted by each of the at least two IR light sources is coaxial with an optical axis of a different one of the at least two image capture units. In these embodiments, when the system also comprises at least one visible light source, each of the at least two image capture units can comprise any combination of image capture units configured to detect light both within the visible spectral range and the IR spectral range, as described herein above.

In some embodiments, the imagery data may be configured for two-dimensional (2D) and/or three-dimensional (3D) display via one or more 2D and/or 3D display devices of one or more displaying types. The one or more display devices may include, for example, one or more of: a head mounted display (HMD); a screen; and/or a hologram.

In some embodiments, the system can be configured as or serve as a diagnostic microscope. In some embodiments, the system can be configured as or serve as a slit lamp microscope. In some embodiments, the system can be configured as or serve as an exoscope (e.g., a surgical digital microscope). In these embodiments (e.g., the diagnostic microscope, slit lamp microscope, and exoscope embodiments), the system can comprise the display and/or output the imagery data to an external display.

In some embodiments, the system can be part of a traditional optical microscope with optical eyepieces. In these embodiments, the display can be embedded in a mono or a stereoscopic eyepiece of the optical microscope (for example, a traditional surgical microscope), or can be external to the microscope.

In some embodiments, the system can be part of a robotic surgery system. In these embodiments, the display can be part of the robotic surgery system or can be external to the robotic surgery system.

According to some embodiments, the IR light emitted from at least one of the at least one IR light source may be collimated at the exit of the IR light source or after one or more other optical elements, before reaching the body part portion.

In some embodiments, the system may be configured for eye surgery where the eye is the body part of a subject being operated. In those cases, a portion of the eye that may be the focus of surgical attention may be the eye's pupil, iris, cornea, retina, lens and/or the area enclosed by the limbus of the eye. The IR illumination/radiation also enables light to reach and return from deeper elements of the eye such as the lens and the retina that can be imaged in a more detailed manner. Moreover, IR light has a better penetration through scattering medium such as cataracted lenses.

In cases the system is used for cataract surgeries or diagnosis, the surgeon/physician/analyst may require a high-quality image of both external, frontal, rear and internal parts of the eye such as the cornea and lens of the eye, for improving surgery and/or diagnosis accuracy, where the quality can be measured in terms of contrast, depth of field, resolution tissues visibility, coloration and coloration contrasts, etc.

The system may be used or embedded in a microscope device where parts thereof are used for the microscope such as lens(es), where the surgeon/physician/analyst may be enabled to view 2D and/or 3D images at least of the portion of the body part being illuminated, in real time or near real time from an eyepiece of the microscope, from a screen and/or from a head mounted display (HMD) device worn by the surgeon/physician.

Figure 13A:
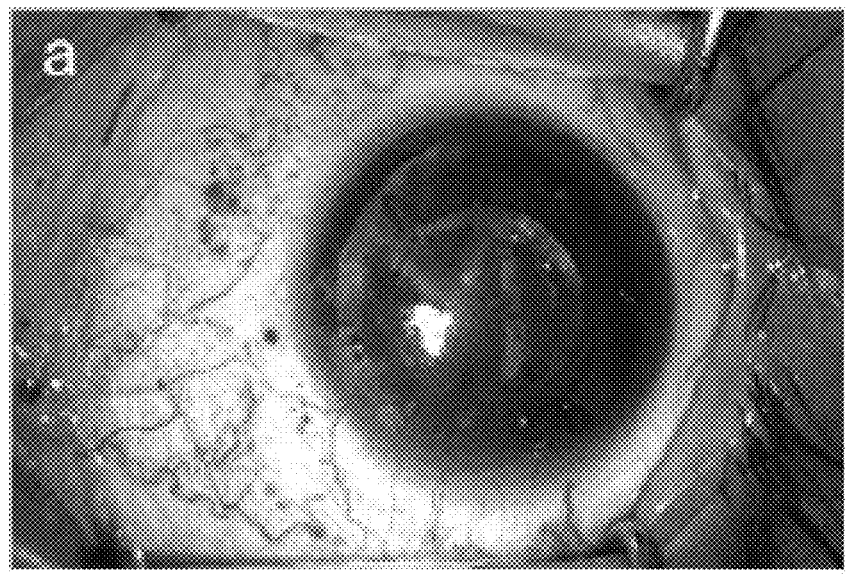
FIGS. 13A and 13B show images of an eye of a subject.
Figure 13B:
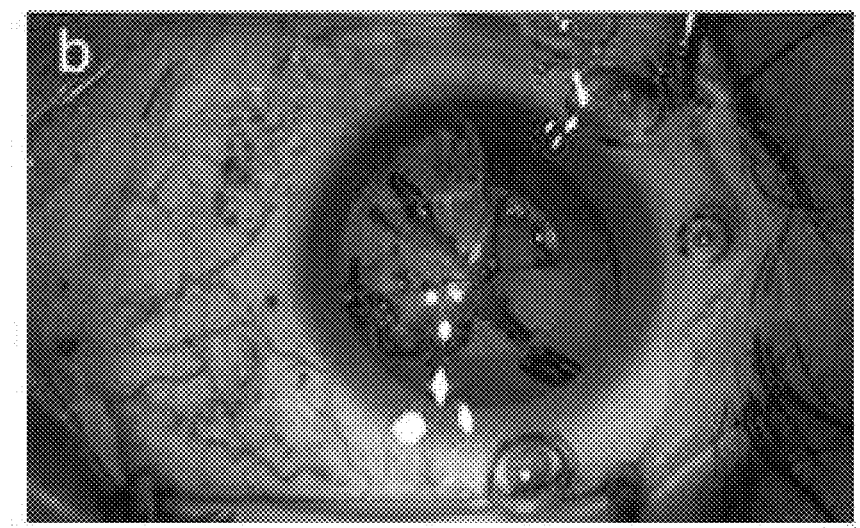

FIG. 13A shows an image of a subject's eye when illuminated only in visible light, while FIG. 13B shows the same eye of the subject while illuminated also with coaxial IR light in a system according to some embodiments. In these embodiments the IR light is coaxial with an optical axis of the image capture unit which is a camera capable of sensing light in the IR as well as in the visible spectra. As can be seen in the FIG. 13B, the IR light illuminates only a portion of the eye, which is roughly the area enclosed by the limbus (e.g., the area illuminated by IR is actually slightly larger than the limbus, and includes also part of the sclera and the eyelid to the right of the limbus in the figure). It is clear from those two images that using the coaxial IR illumination dramatically improves the visibility of the inner parts of the eye such as the fragments of the eye's lens (e.g. during cataract surgery).

According to some embodiments, the system may be used for diagnostical purposes such as for diagnosis of cataract, eye tumors, retinal disease, and the like in addition to or instead of being used for surgical purposes.

The system may also include a focusing mechanism and/or an aperture adjustment mechanism (e.g. as part of the optics of the image capture unit) used to account for changes in illumination. The focus and/or aperture may be adjustable automatically and/or manually in response to or in conjunction with changes in the IR and visible illumination. For example, when the illumination is automatically changed, for instance based on identifying the stage of the procedure (e.g., by image processing, using machine learning, etc.) the focus and/or aperture can also be automatically adjusted to fit the wavelength (e.g., the spectra) of the current illumination.

Aperture diameter may affect the depth of field and the amount of light that is sensed by the image capture unit. In some embodiments, when both IR and visible illumination are used, it may be advantageous to adjust the aperture of the image capture unit (e.g. camera) to a smaller diameter, so that both the area that is illuminated by IR light and the area that is illuminated by visible light are in focus (since the focusing distance of light in different wavelengths is different, and decreasing the aperture diameter increases the depth of field). In some embodiments, when only one of the IR and visible illumination is used, it may be advantageous to adjust the aperture to a larger diameter, so more light is sensed by the image capture unit. In some of these embodiments, when light is switched between IR and visible light when the aperture is larger and the depth of field is smaller, the focus can be manually or automatically adjusted to fit the wavelength.

According to some embodiments, the IR illumination may be within the near IR (NIR) spectrum.

In embodiments in which the system comprises at least one visible light source, the at least one image capture unit may include any combination of one or more image capture units configured to detect light within the visible and the IR spectral ranges. In some embodiments a single image capture unit can be used for sensing both visible and IR light (as one example, an RGB CMOS sensor that senses light from 400 to 1100 nm, or as another example, an RGB-IR CMOS pixel array sensor that can capture RGB and IR images in one sensor).

According to some embodiments, different sensors and/or different image capture units may be used for the IR spectrum and for the visible spectrum. or, for instance in a stereoscopic digital microscope, two cameras, each sensing both visible and IR light).

In some embodiments, the at least one image capture unit may include one or more of:
- at least one RGB sensor, in which the RGB pixels can also detect light in the IR range (e.g., any sensor can be a standard packaged part or in a bare die format, and also in a chip that also comprises a light source or light sources);
- separate sensors for different colors such as one red sensor, one blue sensor, and one green sensor, where the sensors may also be in a different color space, such as Cyan, Magenta, and Yellow;
- at least one RGB-IR camera, which enables simultaneous sensing of light in the visible and at least part of the IR spectrum, in which there are dedicated RGB and IR pixels;
- at least one RGB camera and at least one IR camera.

In some embodiments, when the system is a stereoscopic system (e.g., the body part is imaged by two cameras and the display is a 3D display), for instance in a stereoscopic digital microscope, at least two cameras (e.g., image capture units) are utilized, one for the left channel and the other for the right channel. In these embodiments, when the system comprises at least one visible light source, the at least one image capture unit comprises at least two image capture units, each including any combination of one or more image capture units configured to detect light within the visible and the IR spectral ranges. For example, each of the two image capture units can be configured as any one of the above embodiments (e.g., two RGB cameras, two sets of separate sensors for several spectral ranges, two RGB-IR cameras, two pairs of an RGB camera and an IR camera). According to these embodiments, the at least one IR light source may include at least two IR light sources, each IR light source being coaxial with a different one of the cameras capable of sensing IR light.

According to some embodiments, several image capture units, sensing within the IR spectrum may be used, the at least one IR light source may include several IR light sources, and at least one of the at least one IR light source can be coaxial with one image capture unit.

According to some aspects of some embodiments, there is provided a method for imaging a body part during a medical procedure that may include the following steps:
- illuminating at least a portion of the body part with light in the infrared (IR) spectrum, using at least one IR light source such that IR illumination of at least one of the at least one IR light source is coaxial with an optical axis of an image capture unit that is configured and positioned to detect light reflected from at least a portion of the body part;
- sensing light that is reflected from at least part of the body part, using at least one image capture unit for imaging of the body part, wherein the image capture unit is configured to sense light at least in the IR spectrum; and
- outputting imagery data emanating from the at least one image capture unit for displaying thereof.

The method may further include the step of illuminating the body part with visible illumination, using at least one visible light source, configured to output light in the visible spectrum and balancing between visible illumination from the at least one visible light source and IR illumination from the at least one IR light source, e.g., by controlling the intensity of at least one of the at least one visible light source and/or at least one of the at least one IR light source.

According to some embodiments, the at least one visible light source may include at least one coaxial visible light source (coaxial with respect to the optical axis of a respective camera, the same camera for sensing the IR light and the visible light or a separate sensor or sensors for sensing the visible light). According to these embodiments, when the system comprises more than one image capture unit capable of sensing light in the visible range, the system can comprise at least one visible coaxial light for each of these image capture units.

According to some embodiments, the at least one image capture unit ay include at least two image capture units for stereoscopic imaging, where the at least one IR light source comprises at least two IR light sources, wherein IR light emitted by each of the at least two IR light sources is coaxial with an optical axis of a different one of the at least two image capture units.

According to some embodiments, the at least one visible light source may include at least one visible flood light source. Flood light may be non-coaxial or oblique with respect to the optical axis of the camera. According to these embodiments, when the system comprises more than one image capture unit for sensing light in the visible range, the system can comprise a single visible flood light source (for example in a stereoscopic microscope, a single visible flood light source can be utilized for illuminating the body part imaged by two cameras), or several visible flood light sources.

According to some embodiments, the balancing between visible illumination from the at least one visible light source and IR illumination from the at least one IR light source may be done manually and/or automatically.

According to some embodiments, the imaging data may be processed to alter the appearance of one or more images of the imagery data, for instance by performing debayering, histogram equalization, sharpening, color correction, and the like. In some embodiments, the processing may increase the resolution, the contrast, or the gamma curve of the image. In some embodiments the processing may transform the colors of the image. Color transformations can be performed via an equation or via a lookup table.

The raw imagery data outputted from the at least one image capture unit may be one or more images of the body parts or one or more portions thereof such as, for example a real time (live) video imagery of the subject's body part.

The method may also include the step of collimating IR light emitted from tat least one of the at least one IR light source.

According to some embodiments, the method may also include the step of using a focusing mechanism and/or an aperture adjustment mechanism to account for changes in illumination, wherein the focusing mechanism and/or aperture may be adjustable through one or more automatic and/or manual adjustors in response to changes in the IR and visible illumination.

The term "subject" used in this document may refer to any human or animal subject and/or any human or animal organ, and/or any human or non-human tissue part or any other organic substance or entity.

The term medical procedure may refer to any procedure requiring imaging of one or more body parts such as surgery, diagnosis imaging, non-intrusive procedures etc.

Figure 11:
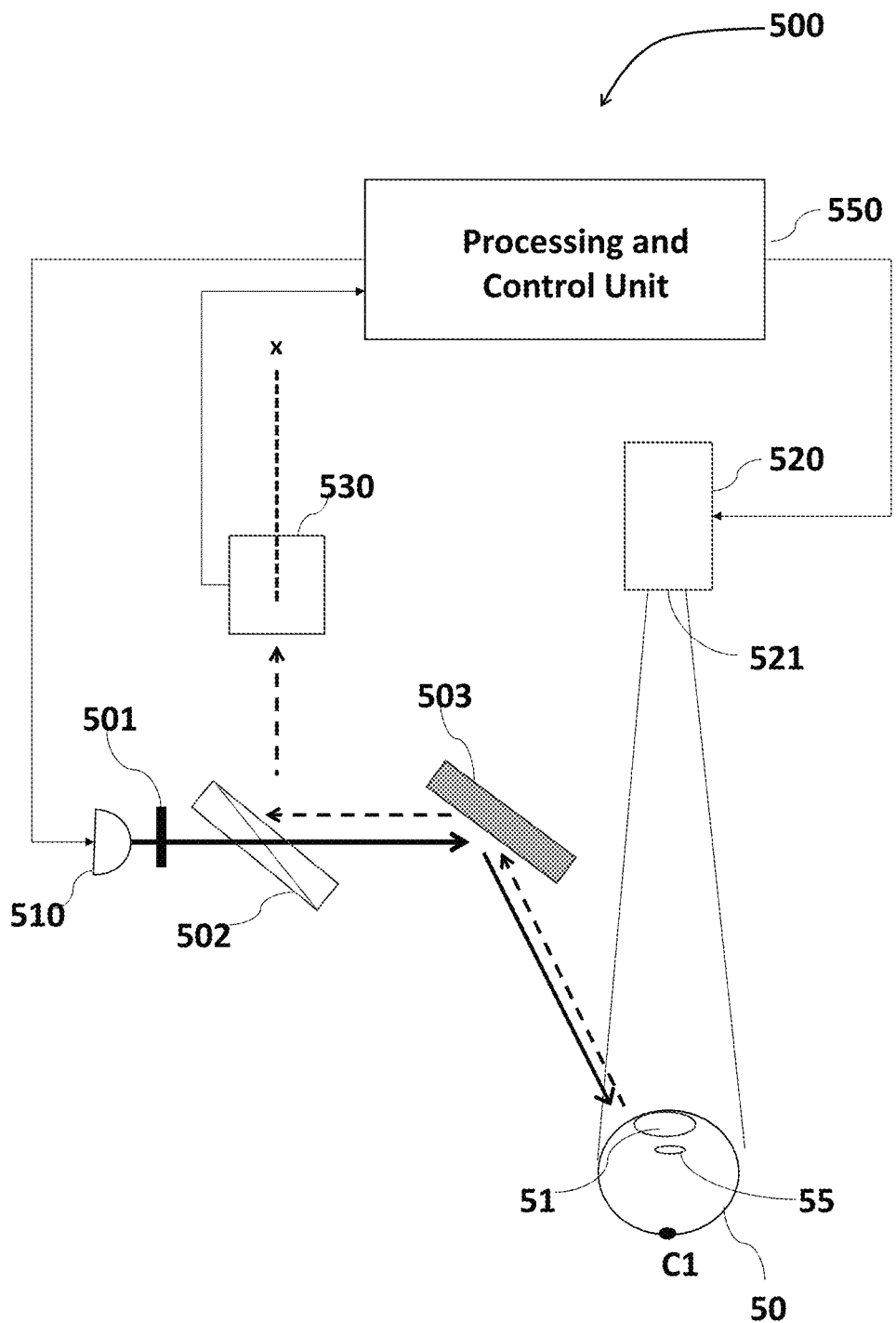
FIG. 11 is a schematic illustration of a system for illuminating of a body part during a medical procedure, using a single IR and visible light sensing image capture unit, according to some embodiments.

Reference is now made to FIG. 11, schematically illustrating a system 500 for imaging a body part of a subject, according to some embodiments. The body part in this example is an eye 50 of a human subject. The system may include:

- an IR light source 510, including one or more IR emitters such as one or more NIR light emitting diode (LED) emitters or superluminescent diode (SLD) or a filtered broadband light source.
- a flood light source 520 configured and positioned to illuminate the body part in a flood light within the visible spectra (e.g., white light emitted at a large aperture), the flood light visible light source 520 may enable adjustment of an output aperture 521 thereof e.g., to fit a size of the body part 50 being imaged;
- an image capture unit 530 such as an RGB camera capable of sensing light both in the visible range and the IR range;
- collimator 501 for collimating the outputted IR light, outputted from the IR light source 510, outputting a collimated beam (for example, since a collimated beam is better focused on the retina and thus the reflected red-reflex is maximized e.g., during eye surgery or examination, the viewer can see some parts of the eye only via the light that is reflected from the retina).
- a beam splitter 502 for allowing at least part of the emitted IR light to pass through it towards mirror 503 (e.g., and from there towards the body part), and also for allowing at least part of the light reflected from the body part (e.g., and from mirror 503) to be reflected towards camera 530.
- a mirror 503 for reflecting the emitted IR light that passed the beam splitter towards the body part and for reflecting light (e.g., IR light and visible light) reflected from the body part towards beam splitter 502.

In this case, the IR and visible light illuminating the eye 50 and/or a portion thereof, is reflected from the mirror 503, which redirects the return light to the beam splitter 502, which in turn, directs the return light to the image capture unit 530.

According to some embodiments the at least one image capture unit may be positioned such that light reflected from the at least a portion of the body part is directed towards the image capture unit such that it is parallel to or coaxial with an optical axis of the image capture unit.

The optical setup illustrated in FIG. 11 may be configured as a periscope, in which light reflected from the body part is reflected by mirror 503 towards the beam splitter 502, and from there reflected towards camera 530. It is noted that any other optical setup is possible, including an optical setup in which light reflected from the body part directly passes through a beam splitter towards the camera, or any other optical setup.

In this case, the IR light is directed to illuminate mainly the limbus area 51 of the eye 50 and the flood light is directed to illuminate a larger area of the eye, that includes the limbus area 51.

According to other embodiments, system 500 may not include and not require the visible flood light illumination and therefore the visible light source 520.

A processing and control unit 550 embedded in or external to the system 500 may be used to control one or more properties of the IR and visible illuminations such as one or more of: intensity, directionality, mode (on/off/dimming state), aperture (e.g., a diameter of an aperture coupled to the light source) etc. via one or more control means such as switches, dimmers etc. The processing and control unit 550 can likewise be used to control one or more properties of the camera (e.g., image capture unit), such as one or more of: focus, aperture (e.g., a diameter of an aperture that is part of the camera's optics), gain etc.

In some embodiments, the processing and control unit 550 may also be configured to receive and process raw imagery data from the image capture unit 530 to automatically determine required balancing actions such as intensity adjustment (dimming or undimming and/or on/off switching) to one or more of the flood light visible light source 520 and/or the IR light source 510. For example, the processing and control unit 550 may automatically identify a stage in the surgical workflow (e.g., based on machine learning), and adjust the illumination according to the stage (for example, the user preferences can define which illumination is used during each stage, and/or what is the intensity of each illumination in each stage).

According to some embodiments, the collimator 501 may be positioned right after the output of the IR light source 510 as shown in FIG. 11.

According to some embodiments, as shown in FIG. 11, the image capture unit 530 comprises optics including, for instance, a focusing lens and/or an adjustable aperture. According to some embodiments, the optics may be manually and/or automatically adjustable e.g., by using electromechanical means that can be automatically and/or manually controllable, for instance to adjust the camera's focus or aperture.

Any other optical setup may be used for being able to direct the IR light towards the body part portion and light reflected from the body part towards the image capture unit 530.

According to some embodiments, the positioning of at least some of the other optical elements such as the collimator 501, the beam splitter 502 and/or the reflector 503 may be adjustable in a manual and/or automatic controllable manner.

According to some embodiments, the coloration of the image(s) (raw imagery data) outputted from the image capture unit 530 may be processed to further improve visibility and contrast between different objects within the image.

According to some embodiments the system comprises at least one visible coaxial light source, where in a case of an eye being the body portion, the subject may be required to look towards a specific direction such as towards one of the coaxial visible light sources. According to some embodiments, when the system does not comprise a visible coaxial light source, or when the system comprises a visible coaxial light source, but the user chooses not to turn it on, in a case of an eye being the body portion, the subject may be required to look towards a visible flood light source, the direction of which can be close enough to the optical axis of the camera such that it does not degrade the coaxial illumination and the image quality.

Figure 12:
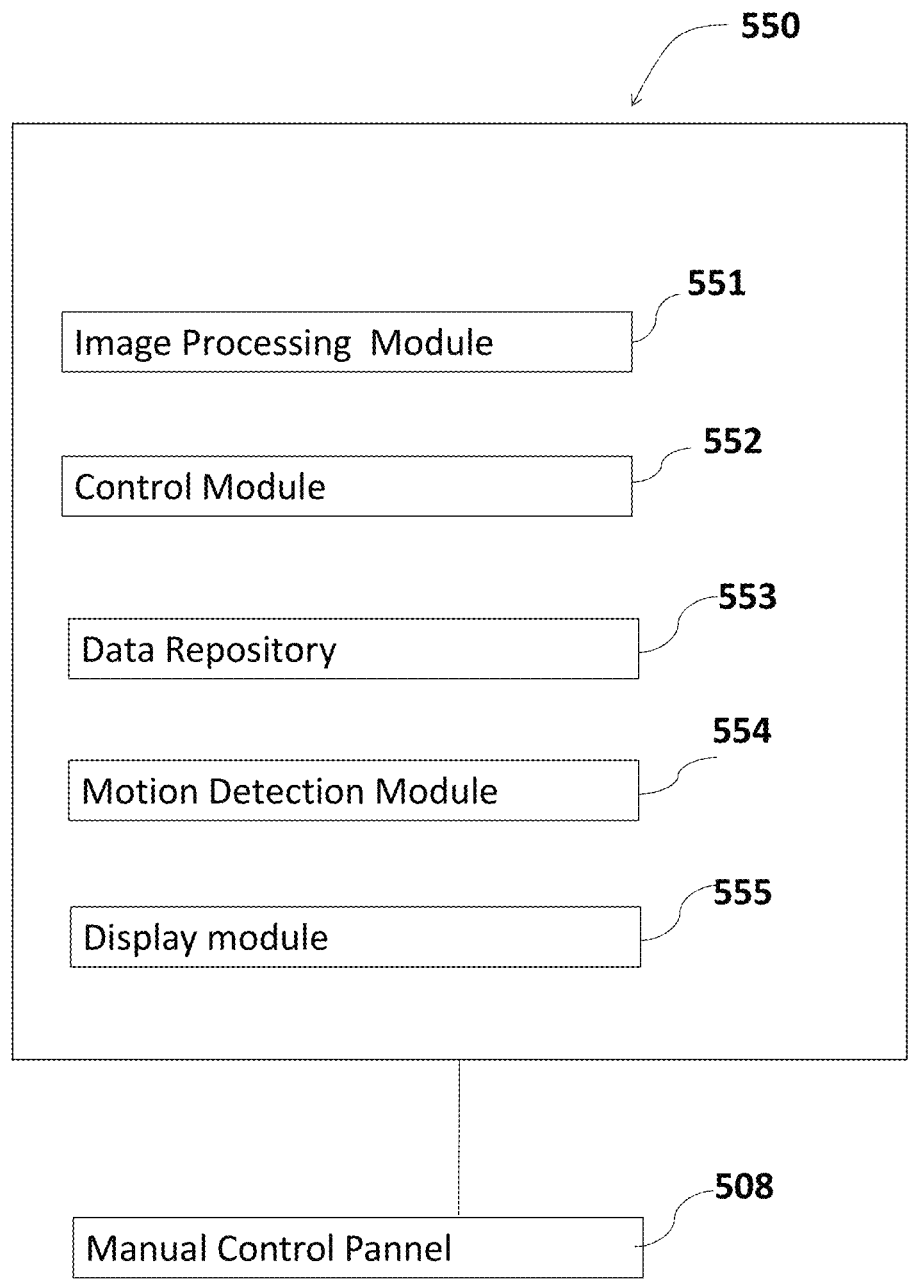
FIG. 12 shows main and optional modules of a processing and control unit of the imaging system of FIG. 11, according to some embodiments.

Reference is now made to FIG. 12, schematically illustrating main and optional modules of the processing and control module 550 of software and/or hardware means, which may include one or more of:
- an image processing module 551, which may be configured to receive raw imagery data of one or more images from the image capture unit 530 and analyze the imagery data for one or more of: (i) identifying of segments of the body part such as in a case of an eye, identification of the limbus, the iris, the pupil etc. (e.g. using image segmentation), identification of tools etc.: (ii) for identification of sensor saturation area(s), out of focusing, and/or undesired reflections in each image, (iii) identification of non-balanced IR vs. visible illumination, for example over illumination (saturation) or under illumination in areas illuminated by one or both illuminations, (iv) processing one or more images of the raw imagery data to improve one or more properties of the processed image(s) such as contrast, visibility, resolution, depth of field, etc., or to alter in any other way the displayable appearance of one or more images or regions of the images of the imagery data, where the image processing module 551 may be configured to output processed imagery data including one or more processed images for displaying thereof to one or more viewers such as one or more professional viewers such as one or more physicians, surgeons, analysts, etc.;

a control module 552, which may enable manual and/or automatic controlling of system properties such as adjusting the camera optics (focus, aperture, etc.), IR and/or visible illumination properties and balancing by controlling one or more properties such as intensity, directionality, aperture etc. for each emitter of each of the IR and/or the visible light sources, where the manual control may be enabled by using one or more control panels of the system 500 such as control panel 508;

a data repository 553 for storage of imagery data, control functions, etc.;

(optionally) a motion detection module 554 for detection of motion of one or more organs or body parts of the subject that is under the medical procedure and/or motion of the physician/surgeon and/or tools of the physician/surgeon;

(optionally) a display module 555 configured for controlling a display of the one or more images of the raw and/or processed imagery data and optionally also for adapting the imagery data to each display device being used such as to a 2D or a 3D display device.

According to some embodiments, the illumination and/or balancing control may be based on image processing results.

Reference is now made to FIG. 14, schematically illustrating a system 700 for imaging a body part such as an eye 70 of a subject, where the system 700 uses two different image capture units 731 and 732 for capturing a left channel and a right channel of the stereoscopic imaging system, and corresponding two different coaxial illumination units 710A and 710B, according to some embodiments. The system may include:

two coaxial illumination units: a first illumination unit 710a and a second illumination unit 710b, each including respectively: an IR source 711A/711B, a visible light source 712A/712B and a dichroic/hot mirror or a beam splitter 714a/714b. The dichroic beam splitter allows the coaxial illumination unit to emit either one of the coaxial IR light and the coaxial visible light, or both;

a single visible flood light source 720 covering an illumination area that includes the body part, the flood light visible light source 720 may optionally enable adjustment of an output aperture 721 thereof e.g., to fit a size of the body part 70 being imaged;

a first collimator 701a and a second collimator 701b, each positioned to collimate, respectively, a first visible and/or IR beam emitted from the first coaxial illumination unit 710a (herein "the first output beam"), and a second visible and/or IR beam emitted from the second coaxial illumination unit 710b (herein "the second output beam");

a first beam splitter 702a and a second beam splitter 702b, each being positioned and configured to allow, respectively, a first beam outputted from the first collimator 701a and a second beam outputted from the second collimator 701b to pass towards mirrors 703a/703b, and to reflect light from the body part (e.g. reflected from mirrors 703a/703b) towards cameras 731/732;

a first mirror 703a and a second mirror 703b, each being positioned and configured to respectively reflect light outputted from the first coaxial illumination unit 710a and the second coaxial illumination unit 710b towards at least a portion 71 of the body part 70 being imaged, and to reflect light reflected from the body part toward beam splitter 702a/702b;

two cameras 731 and 732, each being configured to receive and detect light reflected from a respective first beam splitter 702a and the second beam splitter 702b for imaging at least of a portion 71 of the eye 70; and a processing and control unit 750 which receive image capture units 731 and 732 raw imagery data and is configured at least for processing the raw imagery data and/or for illumination control.

According to some embodiments, the light from each coaxial light unit 710a and 710b may be collimated by collimators 701a and 701b.

Each of the image capturing units 731 and 732 may include optics such as focusing means/lens(es), aperture, etc. one or more of which may be adjustable.

Figure 15:
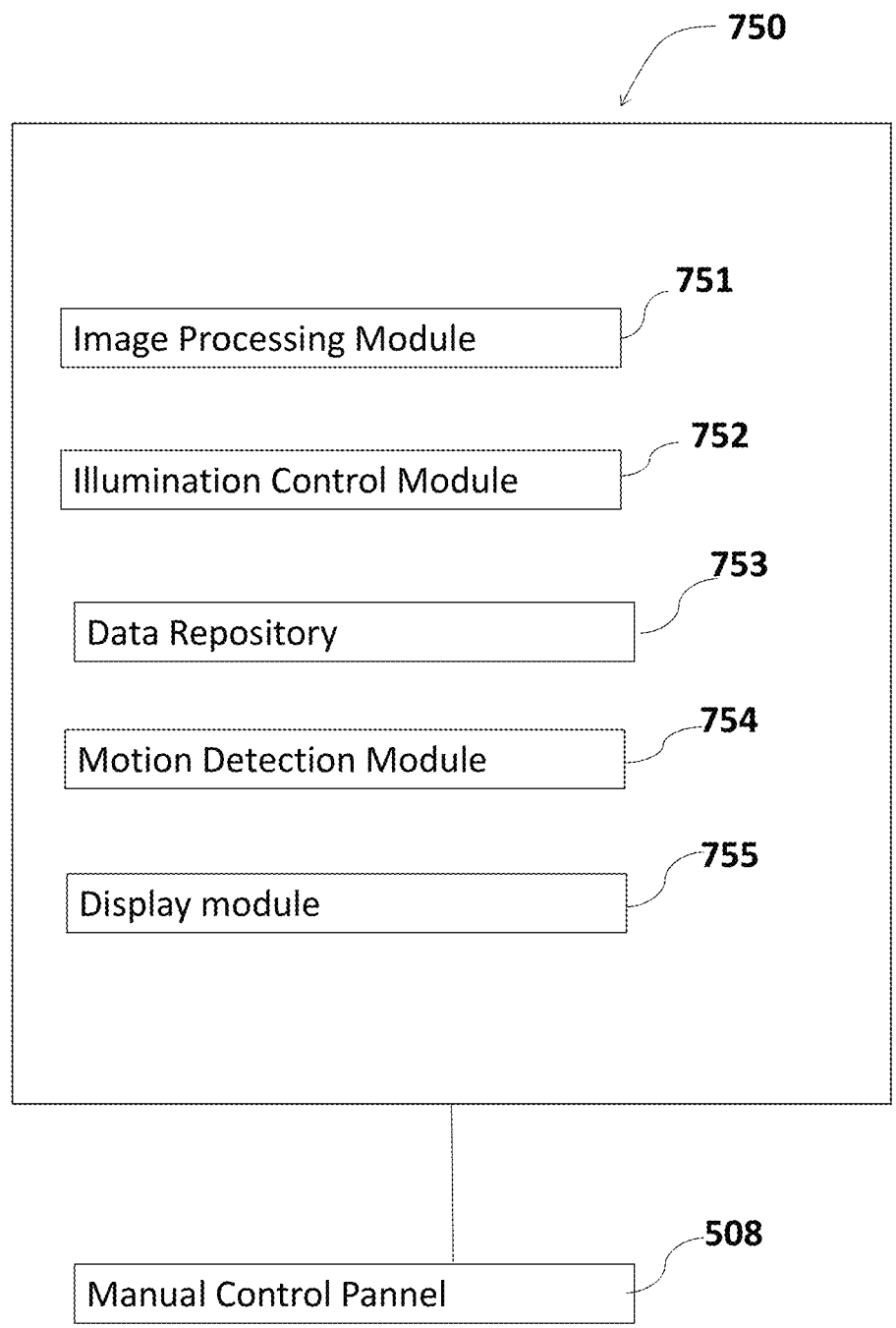
FIG. 15 shows main and optional modules of a processing and control unit of the imaging system of FIG. 14, according to some embodiments.

FIG. 15 schematically illustrates main and optional modules of the processing and control module 750 including one or more of:

an image processing module 751, which may be configured to receive raw imagery data of one or more images from the image capture units 730a and 730b and analyze the raw imagery data for one or more of: (i) identifying of segments of the body part such as in a case of an eye body part, identification of the cornea, the limbus, the iris, the pupil etc. (e.g. using image segmentation), identification of tools etc.: (ii) for identification of sensor saturation area(s), out of focusing, and/or undesired reflections in each image, (iii) identification of non-balanced IR vs. visible illumination, (iv) processing one or more images of the raw imagery data to fit display thereof to one or more display devices and/or to alter in any other way the displayable appearance of one or more images or regions of the images of the imagery data, where the image processing module 751 may be configured to output processed imagery data including one or more processed images for displaying thereof to one or more viewers such as one or more professional viewers such as one or more physicians, surgeons, analysts, etc. via one or more display devices;

a control module 752, which may enable manual and/or automatic controlling of system properties such as optical setup positioning and configuration/arrangement, IR and/or visible illumination properties and balancing by controlling one or more properties such as intensity, directionality, aperture etc. for each emitter of each of the IR and/or the visible light sources, where the manual control may be enabled by using one or more control panels of the system 700 such as control panel 708;

a data repository 753 for storage of imagery data, control functions, etc.;

(optionally) a motion detection module 754 for detection of motion of one or more organs or body parts of the subject that is under the medical procedure and/or motion of the physician/surgeon and/or tools of the physician/surgeon;

(optionally) a display module 755 configured for controlling a display of the one or more images of the raw and/or processed imagery data and optionally also for adapting the imagery data to each display device being used such as to a 2D or a 3D display device.

According to some embodiments, the illumination and/or balancing control may be based on image processing results.

According to some embodiments the balancing control may be done at least by controlling the intensity of any one or more of: the flood light visible light source 720, the first visible light source 712*a*, the second visible light source 712*b*, the first IR light source 711*a* and the second IR light source 711*b*.

According to some embodiments, additional properties of the various light sources can also be controlled, including, for example, one or more of: directionality, aperture, flux, spatial power distribution, color, etc.

Each light source of 711*a*, 711*b*, 712*a*, 712*b* and 720 may include one or more light emitters such as light emitting diode (LED) emitters, lamps with or without filters or a superluminescent diode.

According to some embodiments, the IR emitters of the first and/or second IR light sources 711*a* and 711*b* may be configured to output light in the near IR (NIR) spectrum.

According to some embodiments, the flood light visible light source 720 and/or one or more of the first visible light source 712*a* and the second visible light source 712*b* may be designed to output either white light or light within a narrower bandwidth within the visible spectral range.

According to some embodiments, one or more of the flood light visible light source 720 and/or one or more of the first visible light source 712*a* and the second visible light source 712*b* may include several emitters each configured to output light within a different spectral range within the visible spectral range such as red blue and green. The emitters may be controllable such that each emitter can be operated and controlled (e.g., in terms of intensity) separately, enabling to have only one or several of the overall emitters of the respective light source to be operated or all of them simultaneously.

According to some embodiments, the mirrors 703*a*/703*b* can be excluded from the setup; instead, the image capture units 731/732 can be shifted and tilted such that they capture an identical field of view of the eye (70) through the beam splitters 701*a*/701*b*. By shifting and tilting the image capture units 731/732, one can preserve the coaxiality of the illumination units 710*a*/710*b* and the image capture units 731/732.

Figure 16:
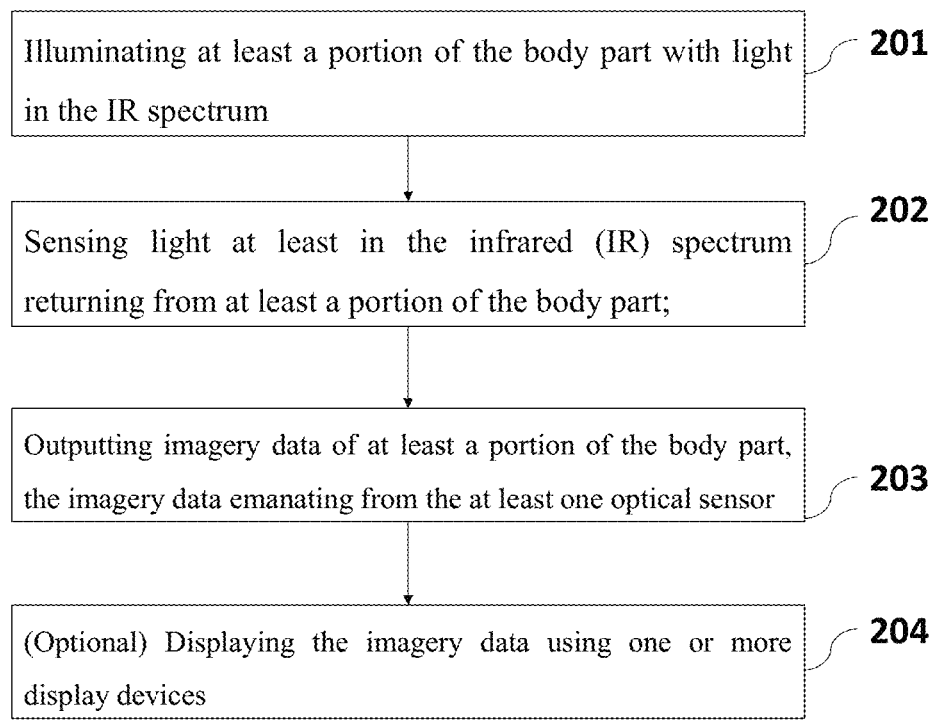
FIG. 16 is a flowchart, schematically illustrating main steps of a method for imaging at least a portion of a body part during a medical procedure, according to some embodiments.

Reference is now made to FIG. 16, showing a flowchart schematically illustrating main and optional steps of a method for imaging a body part of a subject, the method including one or more of the following steps:

illuminating at least a portion of the body part with light in the IR spectrum, using at least one IR light source wherein the at least one IR light source is coaxial in relation to an optical axis of one of at least one image capture unit used for sensing light reflected from at least a portion of the body part being illuminated (step 201);

sensing light at least in the infrared (IR) spectrum reflected from the body part (step 202); and outputting imagery data of at least part of the body part which may include at least part of the portion of the body part being illuminated by the IR illumination or one or more images of an area that includes the body part, the imagery data emanating from the at least one image capture unit for displaying thereof, using one or more display devices (step 203), Optionally the method further includes the step of displaying of imagery data which may be raw imagery data from the at least one image capture unit or processed imagery data via one or more display devices of one or more types (step 204).

Figure 17:
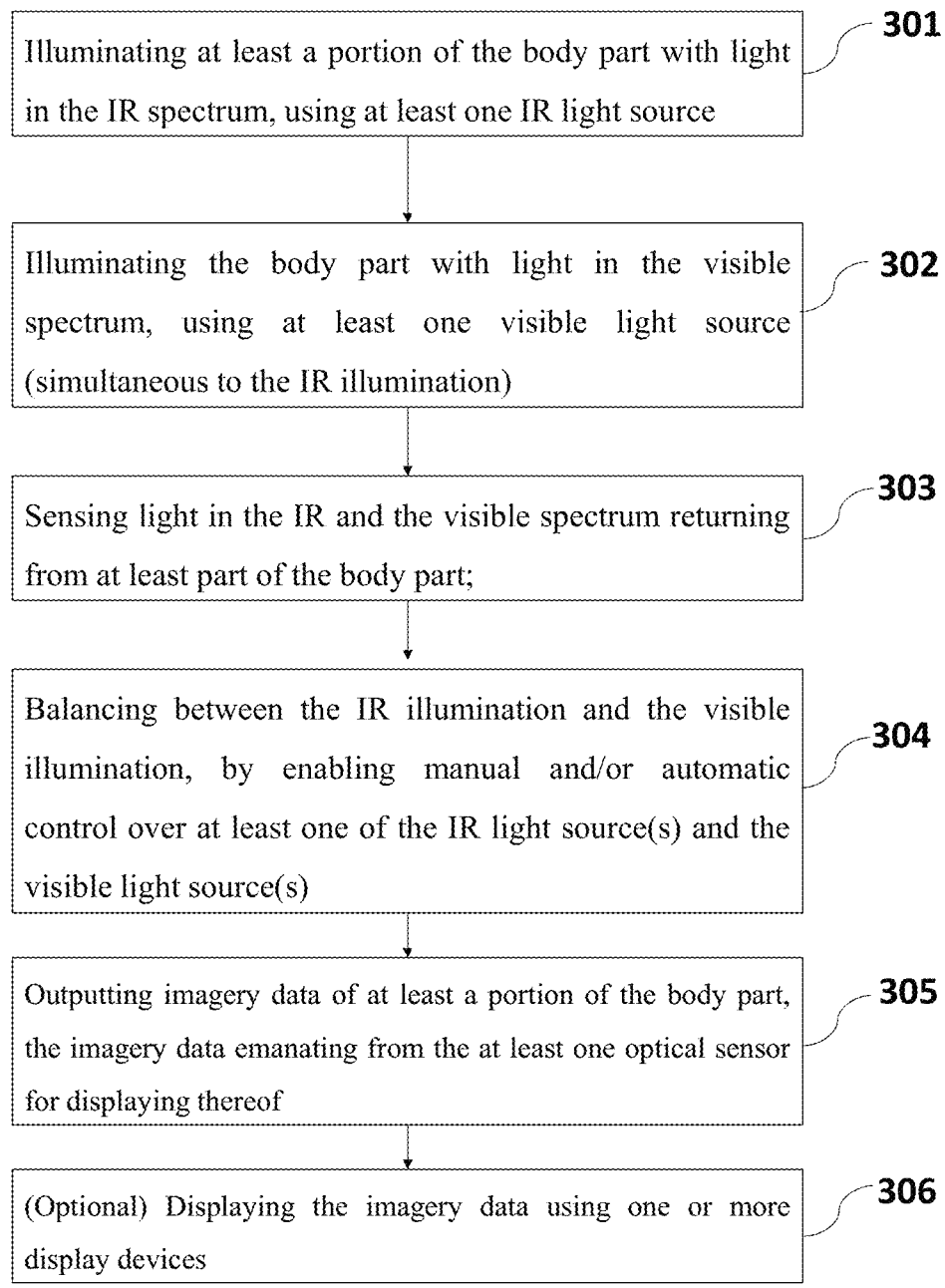
FIG. 17 is a flowchart, schematically illustrating main steps of a method for imaging at least a portion of a body part during a medical procedure, using illumination in the IR and visible spectrums, according to some embodiments.

Reference is now made to FIG. 17 which shows a flowchart schematically illustrating a method for imaging a body part, the method may include one or more of the following steps:

illuminating at least a portion of the body part with light in the IR spectrum, using at least one IR light source (step 301);

simultaneously illuminating the body part with light in the visible spectrum, using at least one visible light source (step 302);

sensing light in the IR and the visible spectra reflected from at least part of the body part (step 303);

balancing between the IR illumination and the visible illumination, by enabling manual and/or automatic control over at least one of the IR light source(s) and/or the visible light source(s) (step 304); and outputting imagery data of at least a portion of the body part, the imagery data emanating from the at least one image capture unit for displaying thereof (step 305).

The method may further include the step of displaying the imagery data using one or more display devices (step 306).

It is to be understood that the presently disclosed subject matter is not limited in its application to the details set forth in the description contained herein or illustrated in the drawings. The presently disclosed subject matter is capable of other embodiments and of being practiced and carried out in various ways. Hence, it is to be understood that the phraseology and terminology employed herein are for the purpose of description and should not be regarded as limiting.

It is appreciated that, unless specifically stated otherwise, certain features of the presently disclosed subject matter, which are, for clarity, described in the context of separate embodiments, may also be provided in combination in a single embodiment. Conversely, various features of the presently disclosed subject matter, which are, for brevity, described in the context of a single embodiment, may also be provided separately or in any suitable sub-combination.

It will be appreciated by persons skilled in the art that the present disclosure is not limited by what has been particularly shown and described hereinabove. Rather the scope of the disclosure is defined by the appended claims and equivalents thereof.

The invention claimed is:

1. A system for imaging a body part during a medical procedure, the system comprising:

at least one image capture unit for imaging the body part, the at least one image capture unit configured to sense light at least in the infrared (IR) spectrum;

at least one IR light source for illuminating a portion of the body part with light in the IR spectrum, wherein IR light emitted by at least one of the at least one IR light source is coaxial with an optical axis of one of the at least one image capture unit, wherein the system is configured to output imagery data emanating from the at least one image capture unit for displaying thereof;

wherein the at least one image capture unit comprises at least two image capture units for stereoscopic imaging, wherein the at least one IR light source comprises at least two IR light sources,
wherein IR light emitted by each of the at least two IR light sources is coaxial with an optical axis of a different one of the at least two image capture units.

2. The system of claim 1 further comprising at least one visible light source for illuminating the body part with light in the visible spectrum, wherein the at least one image capture unit comprises any combination of one or more image capture units configured to detect light within the visible and the IR spectral ranges.

3. The system of claim 2, wherein the system is further configured to enable manual balancing and/or to automatically balance between visible illumination from the at least one visible light source and IR illumination from the at least one IR light source, at least by controlling the intensity of at least one of the at least one visible light source and at least one of the at least one IR light source.

4. The system of claim 2, wherein the at least one image capture unit comprises one or more of:
at least one RGB (Red Green Blue) sensor;
at least one RGB sensor and at least one IR sensor;
separate sensors for different spectral ranges;
at least one RGB-IR sensor.

5. The system of claim 1, wherein the imagery data is processed to alter the displayable appearance of one or more images or regions of the images of the imagery data.

6. The system of claim 1, wherein the imagery data is configured for two-dimensional (2D) and/or three-dimensional (3D) display via one or more display devices of one or more displaying types.

7. The system of claim 6, wherein the one or more display devices comprise one or more of: a head mounted display (HMD); a screen; or a hologram.

8. The system of claim 1, wherein the system is embedded in or serving as one of: (i) a mono or a stereoscopic surgical microscope, (ii) a diagnostic microscope, (iii) a slit lamp microscope, (iv) an exoscope, (v) a control interface of a robotic surgery system, and/or (vi) a traditional optical microscope with optical eyepieces.

9. The system of claim 1, wherein IR light emitted from at least one of the at least one IR light source is collimated.

10. The system of claim 1, wherein the body part includes an eye of a subject and wherein the portion of the body part includes at least one of a retina, a pupil and/or an area enclosed by a limbus of the eye of the subject.

11. The system of claim 1, wherein the medical procedure is a surgery, a cataract surgery, and/or a medical examination.

12. The system of claim 2 further comprising a focusing mechanism and/or an aperture adjustment mechanism, for manually and/or automatically adjusting the focus and/or the aperture of the at least one image capture unit in response to or in conjunction with changes in the IR illumination and/or in the visible illumination.

13. The system of claim 1, wherein the IR illumination is within the near IR (NIR) spectrum.

* * * * *